(12) United States Patent
Zhang et al.

(10) Patent No.: US 8,906,385 B2
(45) Date of Patent: Dec. 9, 2014

(54) INTERFERON-INDUCING PORCINE REPRODUCTIVE AND RESPIRATORY SYNDROME VIRUS ISOLATE

(71) Applicants: Yanjin Zhang, Laurel, MD (US); Yuchen Nan, Greenbelt, MD (US)

(72) Inventors: Yanjin Zhang, Laurel, MD (US); Yuchen Nan, Greenbelt, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 13/692,119

(22) Filed: Dec. 3, 2012

(65) Prior Publication Data

US 2013/0183329 A1     Jul. 18, 2013

Related U.S. Application Data

(60) Provisional application No. 61/565,951, filed on Dec. 1, 2011, provisional application No. 61/655,866, filed on Jun. 5, 2012.

(51) Int. Cl.
| | | |
|---|---|---|
| *A61K 39/12* | (2006.01) | |
| *A61K 39/00* | (2006.01) | |
| *C12Q 1/68* | (2006.01) | |
| *C07K 17/00* | (2006.01) | |
| *C12N 7/00* | (2006.01) | |
| *A61K 39/295* | (2006.01) | |

(52) U.S. Cl.
CPC ....... *A61K 39/12* (2013.01); *C12N 2770/10034* (2013.01); *C12N 7/00* (2013.01); *A61K 2039/543* (2013.01)
USPC .................. 424/204.1; 424/184.1; 424/185.1; 424/186.1; 435/6.1; 530/350

(58) Field of Classification Search
None
See application file for complete search history.

(56) References Cited

U.S. PATENT DOCUMENTS

| | | |
|---|---|---|
| 6,641,819 B2 | 11/2003 | Mengeling et al. |
| 8,383,131 B2 | 2/2013 | Roof et al. |
| 8,481,705 B2 | 7/2013 | Calvert et al. |
| 8,492,132 B2 | 7/2013 | Calvert et al. |
| 2003/0086945 A1* | 5/2003 | Collins et al. ............... 424/204.1 |
| 2008/0233083 A1 | 9/2008 | Ansari et al. |
| 2009/0148474 A1 | 6/2009 | Roof et al. |
| 2011/0150770 A1 | 6/2011 | Bautista et al. |
| 2012/0213810 A1 | 8/2012 | Burgard et al. |
| 2013/0028931 A1 | 1/2013 | Gallei |

FOREIGN PATENT DOCUMENTS

WO      WO/96/36356      11/1996

OTHER PUBLICATIONS

GenBank Accession # JQ087873, Porcine reproductive and respiratory syndrome virus strain A2MC2, complete genome, Jun. 25, 2012.*

* cited by examiner

*Primary Examiner* — Benjamin P Blumel
(74) *Attorney, Agent, or Firm* — Hodgson Russ LLP

(57) ABSTRACT

Provided are polynucleotides and proteins encoded by them which are useful for stimulating an immune response against Porcine reproductive and respiratory syndrome virus (PRRSV) in swine. The compositions can contain a newly discovered PRRSV strain or recombinant versions of it or polynucleotides isolated or derived from it, which can be provided as pharmaceutical preparations.

9 Claims, 6 Drawing Sheets
(3 of 6 Drawing Sheet(s) Filed in Color)

Figure 3

INTERFERON-INDUCING PORCINE REPRODUCTIVE AND RESPIRATORY SYNDROME VIRUS ISOLATE

CROSS-REFERENCE TO RELATED APPLICATIONS

This application claims priority to U.S. provisional patent application No. 61/565,951, filed Dec. 1, 2011, and U.S. provisional patent application No. 61/655,866, filed Jun. 5, 2012, the disclosures of which are incorporated herein by reference.

FIELD OF THE INVENTION

The present invention relates generally to the field of animal health and more specifically to methods and immunogenic compositions for use in swine.

BACKGROUND OF THE INVENTION

Porcine reproductive and respiratory syndrome virus (PRRSV) is a positive-sense single-stranded RNA virus belonging to the family Arteriviridae. It causes an economically important disease, resulting in an estimated $660 million loss per year to the swine industry in the United States. PRRSV appears to inhibit the synthesis of type I interferons (IFNs) in infected pigs. IFNs are not detectable in the lungs of pigs, in which PRRSV actively replicates. PRRSV-infected pigs develop delayed onset and low titer neutralizing antibodies and weak cell-mediated immune responses. Suppression of innate immunity may be an important contributing factor to PRRSV modulation of host immune responses.

PRRSV can be propagated in vitro in an epithelial-derived monkey kidney cell line, MARC-145, and in primary cultures of porcine pulmonary alveolar macrophages (PAMs). PAMs are the main target cells for PRRSV during its acute infection of pigs. PRRSV infection of PAM and MARC-145 cells in vitro leads to a very low expression of interferon-α (IFN-α) for viral strains studied to date.

Type I IFNs, such as IFN-α and -β, are critical to innate immunity against viral infection and contribute to the modulation of adaptive immunity. The innate immune system is activated after cellular pattern recognition receptors (PRR) sense pathogen associated molecular patterns (PAMPs) of invading pathogens. Host PRRs for RNA viruses include Toll-like receptors (TLRs) and RIG-I-like receptors (RLRs). Activation of the TLR or RLR pathways eventually leads to the secretion of type I IFNs. The binding of type I IFNs to their receptors activates the Janus kinase (JAK)-signal transducer and activator of transcription (STAT) pathway, which induces expression of IFN-stimulated genes (ISGs) and results in the establishment of an antiviral state.

Some PRRSV strains suppress IFN-β expression in MARC-145 cells and PRRSV non-structural proteins (nsp) 1, 2, 4, and 11 inhibit IFN induction when over-expressed. PRRSV can also inhibit IFN downstream signaling and expression of ISGs in both MARC-145 and PAM cells. The nuclear translocation of STAT1/STAT2/IRF9 heterotrimers was blocked in PRRSV-infected cells, while the IFN-induced phosphorylation of STAT1 and STAT2 was not affected.

Many efforts to control PRRS have been attempted, but have been unsuccessful. There is thus an ongoing and long felt need for improved compositions for prophylaxis and/or therapy of PRRS.

BRIEF SUMMARY OF THE INVENTION

The present invention provides compositions and methods for use in stimulating an immune response against PRRSV in swine. In general, the compositions comprise novel polynucleotides and/or proteins present in, or derived from, a newly discovered strain of PRRSV which is further described herein. The strain is referred to from time to time in the present disclosure as "A2MC2."

The compositions and methods are useful for, among other functions, stimulating production of neutralizing antibodies against PRRSV, and in certain embodiments, antibodies which also recognize strains of PRRSV that are distinct from the strain that is a subject of this invention.

The invention relates to the discovery of novel nucleotide changes in the genome of the presently presented PRRSV strain, and concomitant amino acid changes resulting from the nucleotide changes. These changes distinguish A2MC2 from other, previously known strains of PRRSV and are believed to be at least in part responsible for unexpected properties of the strain, such as the capability to stimulate production of type I interferons by infected cells.

Novel amino acid changes in A2MC2 are summarized in Table 1. The changes occur in the amino acid sequences of PRRSV proteins Nsp8, Nsp10, Nsp12, and GP3.

In various embodiments, the invention provides isolated and/or recombinant polynucleotides encoding one, or all, or any combination of these amino acid sequences, expression vectors comprising DNA polynucleotides encoding the amino acid sequences, cells comprising the polynucleotides, cells comprising virions encoded by the polynucleotides, isolated preparations of such virions, and pharmaceutical compositions comprising the virions, or the polynucleotides without virions.

In various aspects of the invention, methods of making vaccine preparations, and methods of using vaccine preparations for stimulating an immune response against PRRSV in swine are provided. In general, the method of making the vaccines comprises culturing cells which comprise polynucleotides of the invention, allowing expression of the polynucleotides to produce virions, and isolating the virions from cells in the cell culture and/or from the cell culture media.

The method of the invention involves administering a composition of the invention to a swine (or any other animal that is susceptible to PRRSV infection). The swine may be a swine that is at risk for being infected by PRRSV. The composition is administered via any acceptable route, and can be administered at any time during the life of the swine, and can be administered once, or more than one time. In general, administration of a composition of the invention is followed by production of antibodies by the swine so as to prevent or lessen the severity of PRRS. In one embodiment, the amount of antibodies produced by the vaccinated subject is sufficient to partially, or fully, neutralize PRRSV. Neutralization of PRRSV is understood in the art and can be measured using any acceptable technique.

In particular aspects, the invention provides polynucleotide sequences encoding certain polypeptide amino acid sequences, and proteins comprising the amino acid sequences, and includes at least the following specific embodiments: DNA or RNA polynucleotides which encode at least one amino acid sequence selected from the group of amino acid sequences consisting of SEQ ID NO:1, (Nsp8), SEQ ID NO:2 (Nsp10), SEQ ID NO:3 (Nsp12), SEQ ID NO:4 (GP3; encoded by ORF3), and combinations thereof. The polynucleotide can encode all of these amino acid sequences, or any combination thereof. The polynucleotides can also encode the amino acid sequences of ORF1a (SEQ ID NO:9, which includes Nsp8), ORF1b (SEQ ID NO:10, which includes Nsp10 and Nsp12) and SEQ ID NO:4 (GP3). The polynucleotides can also encode the amino acid sequences of SEQ ID NO:11 (ORF2), SEQ ID NO:12 (ORF4), SEQ ID NO:13 (ORF5), SEQ ID NO:14 (ORF6) and SEQ ID NO:15 (ORF7). The disclosure of each polynucleotide herein includes disclosure of its complementary sequence. Each polynucleotide and amino acid sequence can comprise or consist of the disclosed sequence.

The polynucleotides can be present in a vector, such as an expression vector comprised of DNA. The polynucleotides can be present in a eukaryotic cell in culture, such as an epithelial-derived monkey kidney cell, or a porcine pulmonary alveolar macrophage. In certain embodiments, the isolated or recombinant polynucleotide can be an RNA polynucleotide. The RNA polynucleotide can be present in an isolated PRRSV virion, or in such a virion in cell culture, or such a virion in a pharmaceutical preparation. The virion can comprise any single polypeptide sequence described by the amino acid sequences disclosed herein, or any combination of them.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3. Growth properties of A2MC2 in MARC-145 and PAM cells. A. Multi-step growth curve of A2MC2 in MARC-145 cells. The cells were inoculated with 0.01, 0.1 and 1 multiplicity of infection (MOI) of A2MC2 virus. Virus yields at different time points after inoculation were titrated by an immunofluorescence assay. Error bars represent variation between three repeated experiments. Significant differences in virus yields between 0.01 MOI and the other two groups are denoted by "", which signify a P value of <0.01. B. Plaque assay completed using MARC-145 cells. The cells were infected with diluted A2MC2, VR-2385 or MLV and overlaid with agarose. A plate of mock-infected cells was included as a negative control. Plaques were revealed at 4 dpi and photographed for comparison. C. Cytopathic effect in PRRSV-infected PAMs. PAM cells were inoculated with PRRSV and at 20 hpi, observed using bright field microscopy. Mock-infected cells were included for comparison. PRRSV VR-2385 and NVSL led to cell death and lysis, while A2MC2 and MLV had little cytopathic effect. D. Cell viability assay of PAM cells. PRRSV-infected PAMs were assayed at 20 hpi with CellTiter-Glo kit (Promega). Relative folds of cell viability in comparison with uninfected PAMs were plotted. Only VR-2385-infected cells had significantly lower viability (denoted by "", indicating P<0.01) than uninfected PAMs. A2: A2MC2, NV: NVSL, VR: VR-2385. E. Virus yield titrated using MARC-145 cells. Cell culture supernatant samples from PRRSV-infected PAMs at 24 hpi were titrated in MARC-145 cells by IFA. Median tissue culture infectious dose per ml is shown. Error bars represent variation between repeated experiments. The virus yields of A2MC2 and MLV were significantly lower (denoted by "*", indicating P<0.05) than VR-2385.

DETAILED DESCRIPTION OF THE INVENTION

Figure 1:
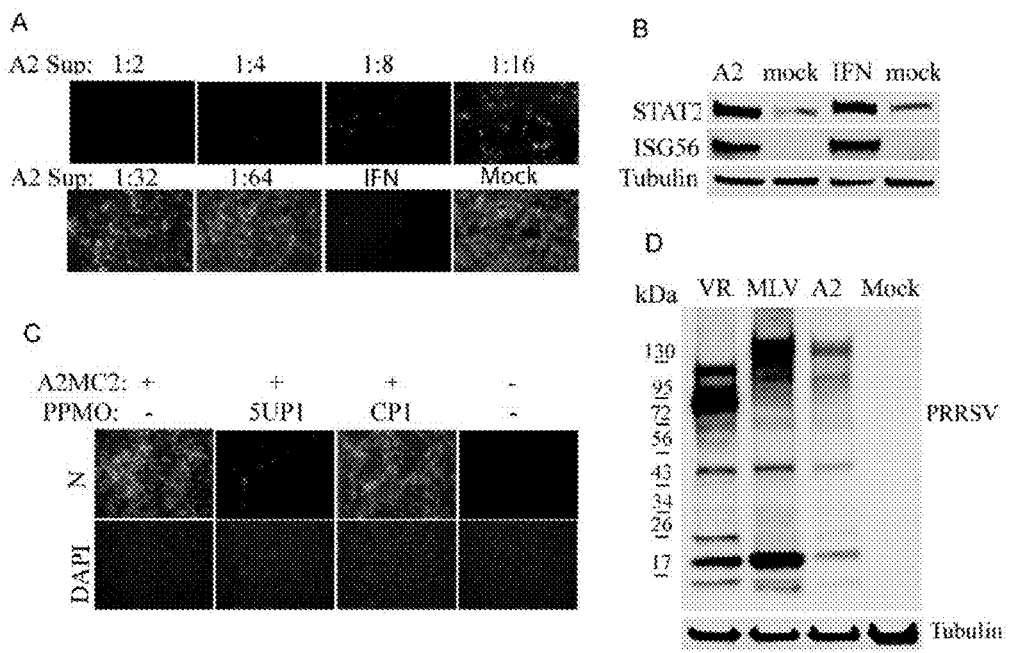
FIG. 1. Detection of antiviral activity in cell culture supernatants from A2MC2-infected MARC-145 cells. A. Inhibition of NDV-GFP replication in Vero cells. Vero cells were treated with dilutions of cell culture supernatant of A2MC2-infected MARC-145 cells. The Vero cells were inoculated with NDV-GFP 12 h after the treatment, and observed under fluorescence microscopy at 24 h post-infection. Treatment of the cells with IFN-α at a final concentration of 1000 U/ml was included as a positive control. B. Elevation of STAT2 and ISG56 proteins in Vero cells after treatment with the supernatant from A2MC2-infected MARC-145 cells detected by Western blot analysis. Vero cells treated with IFN-α and mock-treated were included as positive and negative controls, respectively. Blotting with β-tubulin antibody was done to normalize protein loading. C. Inhibition of A2MC2 replication in MARC-145 cells by PRRSV-specific peptide-conjugated phosphorodiamidate morpholino oligomer (PPMO) 5UP1. A scrambled control PPMO CP1 was included as a negative control. An indirect immunofluorescence assay with PRRSV N-specific monoclonal antibody was conducted. The bottom panel of images shows the nuclear DNA stained with 4',6'-19 diamidino-2-phenylinodole (DAPI). D. Detection of PRRSV proteins in whole cell lysates of A2MC2-infected cells (A2 lane) detected by Western blotting with pig antiserum. Cell lysate samples from PRRSV VR-2385-infected (VR lane) or MLV-infected cells were included as positive controls. Molecular weight markers are illustrated on the left.

The present invention is based at least in part on our discovery of a PPRSV isolate which unexpectedly induces production of type I interferons in cultured cells. This property of the virus was surprising because PPRSV is known in the art to interfere with type 1 IFN signaling. It is believed a similar effect is elicited in infected cells in animals vaccinated with a composition of the invention. We further discovered that this isolate is equal to or superior to certain known PPRSV strains in its capacity to stimulate production of neutralizing antibodies in pigs. Thus, the invention provides compositions and methods for prophylaxis and/or therapy of PPRSV infection in pigs. The compositions include vaccine preparations, isolated virus, polynucleotides encoding viral proteins and virions, isolated cells comprising polynucleotides encoding the virus, and comprising the virus itself, and cell culture media comprising the virus.

Each of the DNA and RNA polynucleotides and viruses provided by the invention can be provided as recombinant, and/or purified, and/or isolated compositions. Each of these compositions can be purified to any desired degree of purity. In certain embodiments, an isolated RNA polynucleotide can be present in isolated viral particles, or it can be in an isolated polynucleotide preparation.

In one embodiment, the invention provides an isolated or recombinant polynucleotide that encodes at least one of the PPRSV amino acid sequences which constitute PPRSV Nsp8, Nsp10, Nsp12 and GP3. The amino acid sequences of these proteins are SEQ ID NO:1 for Nsp8, SEQ ID NO:2 for Nsp10, SEQ ID NO:3 for Nsp12, and SEQ ID NO:4 for GP3. We have discovered that mutations in these amino acid sequences distinguish the present PPRSV strain from other PPRSV strains, such as those referred to in the art as VR2332 and MLV, despite having approximately 99% homology to the viral genomes of these known strains. Table 1 summarizes the amino acid changes. The nucleotide positions presented in Table 1 reflect those nucleotide variations causing the codon change to encode different amino acids shown in the Table. The nucleotide positions are given relative to SEQ ID NO:16, which provides the DNA equivalent (the cDNA) of the RNA genome of the PPRSV strain that is a subject of the present invention. In one embodiment, a virus of the present invention can comprise a genome which comprises or consists of SEQ ID NO:16, wherein each T is replaced by a U. Those skilled in the art will recognize though, that due to the redundancy of the genetic code, there are a multitude of polynucleotide sequences that can encode the PPRSV amino acid sequences disclosed herein. Thus SEQ ID NO:16 is an illustrative example of one polynucleotide sequence, as is its RNA equivalent. Further, certain portions of SEQ ID NO:16 are dispensable for making and using the compositions of the invention, such as the polyA tail. Those skilled in the art will recognize that PPRSV replication is complex and certain viral proteins are produced by, for example, ribosomal frameshifting, by proteolytic processing, or via translation of sub-genomic RNAs. Accordingly, not all viral proteins that are encoded by the viral genome are necessarily components of viral particles, and not all amino acid sequences disclosed herein necessarily represent complete, distinct proteins, depending again on the stage of infection and viral life cycle. For instance, structural proteins encoded by ORFs 2-7 are included into virions, while certain non-structural proteins are not part of the virions and are synthesized only after infection.

The polynucleotide of SEQ ID NO:16 encodes eight open reading frames (ORFs) of the A2MC2 strain of PPRSV that is a subject of this invention. These are termed ORF1a (SEQ ID NO:9), ORF1b (SEQ ID NO:10), ORF2 (SEQ ID NO:11), ORF3 (SEQ ID NO:4, also referred to herein as GP3), ORF4 (SEQ ID NO:12), ORF5 (SEQ ID NO:13), ORF6 (SEQ ID NO:14) and ORF7 (SEQ ID NO:15). In the present invention, the sequence of Nsp8 comprises the C-terminus of ORF1a, while Nsp10 and Nsp12 are both part of ORF1b. SEQ ID NO:16 and amino acid sequences encoded by it are also presented in GenBank under accession number JQ087873, Aug. 23, 2012 entry, which is incorporated herein by reference. In certain embodiments of the invention, a recombinant or isolated DNA or RNA polynucleotide encodes all of the proteins encoded by SEQ ID NO:16. Representative and non-limiting polynucleotide sequences encoding the amino acid sequences of PPRSV Nsp8, Nsp10, Nsp12 and GP3 are provided as SEQ ID NO:5, SEQ ID NO:6, SEQ ID NO:7 and SEQ ID NO:8, respectively. It will be apparent to those skilled in the art that representative polynucleotide sequences encoding ORF1a, ORF1b, ORF2, ORF3, ORF4, ORF5, ORF6 and ORF7 are present and readily ascertainable from SEQ ID NO:16, which presents the entire genome of a virus that is a subject of the present invention.

In one embodiment, the invention provides an isolated polynucleotide comprising a DNA sequence encoding an RNA polynucleotide, wherein the RNA polynucleotide encodes at least one of the PPRSV proteins Nsp8, Nsp10, Nsp12 and GP3 disclosed herein.

In certain embodiments, the invention provides recombinant or isolated polynucleotides which encode PRRSV proteins comprised by PRRSV virions, which can be replication competent virions, or replication defective virions. Replication competent virions contain all necessary polynucleotide sequences and proteins for virion synthesis. They are capable of continuing to propagate themselves and to infect other cells once infection occurs. Replication defective virions contain polynucleotide sequences and proteins necessary for infecting target cells but cannot continue to propagate themselves and infect other cells.

The PRRSV virions (e.g., viral particles) can be achieved, for example, by expression of an RNA molecule provided by the invention in a eukaryotic cell. In certain embodiments, the RNA molecule can be encoded by and expressed from a DNA molecule provided by the invention. Infected cells are cultured for a period of time during which PRRSV is produced. PRRSV produced accordingly can be extracted from the cells and/or the cell culture media using conventional techniques, given the benefit of the present disclosure. Thus, the invention includes cell cultures, wherein the cells comprise DNA and/or RNA encoding the novel amino acid sequences of the invention, which may be part of replication competent virions. The invention also includes cell culture media that contains the novel PPRSV viruses described herein. The invention further includes propagating and/or isolating cultured progeny of viruses of the invention.

In certain embodiments, the isolated or recombinant polynucleotides provided by the invention encode at least two, three or all four of the PPRSV proteins Nsp8, Nsp10, Nsp12 and GP3 as disclosed herein. In particular embodiments, cell cultures comprising the recombinant polynucleotides and all four of these proteins of the invention are provided.

In an embodiment, a polynucleotide of the invention can encode amino acid sequences for any one, all or any combination of SEQ ID NO:11 (ORF2), SEQ ID NO:4 (GP3, also known as ORF3), SEQ ID NO:12 (ORF4), SEQ ID NO:13 (ORF5), (SEQ ID NO:14 (ORF6) and (SEQ ID NO:15-ORF7). Accordingly, the invention also provides isolated PPRSV virions comprising these amino acid sequences, as well as compositions comprising such virions, which may be formulated as pharmaceutical formulations suitable for administration to swine.

In one embodiment, the invention provides a recombinant DNA vector which includes a polynucleotide which encodes at least one protein selected from the group consisting of Nsp8, Nsp10, Nsp12 and GP3 disclosed herein, and combinations thereof. In one embodiment, the recombinant vector comprises polynucleotide sequence encoding all of the Nsp8, Nsp10, Nsp12 and GP3 amino acid sequences disclosed herein. In one embodiment, the recombinant vector is a replication competent viral vector (i.e., contains polynucleotide sequences encoding proteins that are sufficient to propagate the virus in certain cell cultures), but may be replication-defective in a target cell type. In one embodiment, the recombinant viral vector is a porcine adenovirus vector. Other, commercially available mammalian expression vectors, such as pCDNA3, pCAMV-Tag, pEGFP and pCAGEN can also be used to contain and express the viral proteins. In one embodiment, the pCAGEN vector available from Addgene can be modified to comprise any of the polynucleotides described herein. In an embodiment, the vector constitutes an infectious clone.

One aspect of the invention entails producing and/or recovering recombinant infectious clones. In certain embodiments, the method includes producing and/or recovering, or isolating viral particles, such as from a cell culture. The method comprises infecting susceptible cells in culture with a recombinant viral vector of the invention and thereafter recovering the viral particles from the culture media, or supernatant, etc., using any technique known in the art. In various aspects, the infected cells are epithelial-derived monkey kidney cells, such as the cell line known as MARC-145, or are primary cultures of porcine pulmonary alveolar macrophages (PAMs). Such cells which comprise polynucleotides and/or viral particles disclosed herein are encompassed within the invention. In one embodiment, a virus of the invention does not cause cytopathic effects after infection of PAM cells. In one embodiment, a composition of the invention induces elevation of IFN-β transcripts in MARC-145 cells which is from 50 to 820 fold (including all ranges and sub-ranges there between) higher than that induced by strains VR-2385, VR-2332, NVSL, or MLV in MARC-145 cells.

In one aspect, the invention provides a vaccine formulation for use in stimulating an immune response. The immune response can comprise an innate, humoral, or cell-mediated immune response, or combinations thereof. In one embodiment, the stimulated immune response comprises induction of IFN-1 production, or an increase of IFN-1 production relative to a reference. In another embodiment, the stimulated immune response comprises stimulation of antibodies that can neutralize PRRSV. In certain variations of the invention, the stimulated immune response can comprise production of an equal amount, or more neutralizing antibodies than a reference, such as the amount of neutralizing antibodies that are produced by introducing VR2332 or MLV into a test animal. The invention also provides for stimulating production of antibodies that recognize more than one strain of PPRSV. In one embodiment, the invention results in production of the same or a greater amount of neutralizing antibodies that produced by vaccination using VR2332 or MLV.

In one aspect, the invention pertains to vaccinating pigs against the U.S. form of PPRSV. In certain embodiments, the method involves treating or reducing the severity of or incidence of PRRSV infection. Treating or reducing the severity of or incidence of PRRSV can comprise reducing the severity of clinical and/or pathological signs normally associated with infection, and can include prevention of such signs and/or symptoms. Some examples such signs include but are not necessarily limited to anorexia, skin discolorations, lethargy, respiratory signs, and coughing in young pigs, and mummified piglets or abortion in sows.

In general, the method of the invention comprises administering to one or more porcine subjects (i.e., pigs) a composition comprising isolated virus of the invention, or recombinant virus of the invention (i.e., virus produced by a recombinant expression vector) or a viral vector provided by the invention. Such compositions can comprise a carrier and/or veterinarily/pharmaceutically acceptable vehicle or excipient, including but not limited to diluents, stabilizers, preservatives, pH buffering agents, viscosity enhancing additives, saline and/or a phosphate buffer. The administration elicits in certain embodiments neutralizing antibodies against PRRSV. In particular examples, the neutralizing antibodies can be detected in a sample obtained from the animal two to four weeks after vaccination. In certain embodiments, neutralizing antibodies to more than one strain of PRRSV are raised.

The compositions described herein may be formulated for administration via any acceptable route. In certain embodiments, the formulations are suitable for and are administered via oral, nasal, intramuscular, subcutaneous, or intradermal delivery. In one embodiment, the formulation can be suitable for forming an aerosol. The formulations provided herein can further comprise additional immunogenic compositions, such as other PRRSV strains or immunogenic portions thereof, and/or at least one immunogen from at least one additional, non-PRRSV swine pathogen. Any of the vaccines in the present invention also may comprise an adjuvant. An "adjuvant" is any substance added to a vaccine to increase the immunogenicity of the vaccine.

In specific embodiments, pigs can be vaccinated with a composition of the invention at any time. In some non-limiting examples, a composition of the invention is administered to a neonatal, juvenile or adult pig at any time during their lives. In non-limiting embodiments, piglets can be vaccinated within a day of birth, or between the first and fourth weeks of life. Female pigs can be vaccinated before, during or after pregnancy. Any swine can be boosted, such as by a series of two or more vaccinations administered over a period of time. All, or only some members of any particular pig population can be vaccinated. In some embodiments, only some pigs are vaccinated and others acquire immunity to more than one PRRSV strain by contact with the vaccinated animals. The invention is expected to be suitable for vaccination of any type of swine or other mammal that is susceptible to PRRSV infection.

The dosage for all routes of administration of compositions of the invention can depend on various factors including, the size, age, gender and health of the pig. In certain embodiments the method involves administering an effective amount of a composition of the invention. An effective amount can comprise an amount of the composition sufficient to prevent or reduce the severity of clinical and/or pathological signs normally associated with PRRSV infection, such as anorexia, skin discolorations, lethargy, respiratory signs, mummified piglets, coughing, or combinations thereof. In one embodiment, an effective amount is an amount sufficient to induce production of neutralizing antibodies. In certain embodiments, an effective amount is $10^5$ of 50% Tissue Culture Infective Dose (TCID50) for intramuscular or intranasal administration.

In one embodiment, the composition of the invention comprises an attenuated PRRSV virus, the genome of which encodes at least one of the novel PRRSV proteins disclosed herein, and can encode all or any combination of the novel PRRSV proteins disclosed herein. By attenuated it is meant that subsequent to administering the virus to a swine or other mammal prone to PRRSV, clinical signs of PRRSV disease do not arise or are less than in an unvaccinated infected animal, but an immune response against pathogenic forms of PRRSV is stimulated. Attenuation of a virus can be achieved by any of a variety of well-known methods. In certain embodiments, an isolated or recombinant virus of the invention is attenuated by passaging at least 36 times in cell culture, or by engineering point mutations in the viral genome, or by gene swapping.

The following examples are presented to illustrate the present invention. They are not intended to limiting in any manner.

EXAMPLE 1

This Example provides a description of the PRRSV that is a subject of the present invention and its capability to stimulate product of type 1 IFNs.

PRRSV is known to interfere with the signaling of type I IFNs. Here we found PRRSV A2MC2 induced type I IFNs in cultured cells. A2MC2 replication in MARC-145 cells resulted in the synthesis of IFN-α2 protein, transcript elevation of the IFN-stimulated genes ISG15 and ISG56, and the proteins of the signal transducer and activator of transcription 2 (STAT2) and ISG56. A2MC2 infection of primary porcine pulmonary alveolar macrophages (PAMs) also led to the elevation of the two proteins, but had little cytopathic effect. Furthermore, A2MC2 infection of MARC-145 or PAM cells had no detectable inhibitory effect on the ability of IFN-α to induce an antiviral response. Sequencing analysis indicated that A2MC2 was closely related to VR-2332 and Ingelvac PRRS MLV with an identity of 99.8% at the nucleotide level.

Detection of Antiviral Activity in Cell Culture Supernatant from A2MC2-Infected MARC-145 Cells In studying PRRSV interference of IFN signaling, we discovered one PRRSV cell culture isolate that did not inhibit IFN signaling but induced antiviral activity in MARC-145 cells. After plaque purification of this isolate three times, one plaque was named A2MC2.

Vero cells are not susceptible to PRRSV infection and were used as an indicator cell line for the studies. NDV-GFP is sensitive to type I IFNs, so pre-treatment of Vero cells with IFN-α inhibited NDV-GFP replication and was included as an assay control. Treatment of Vero cells with dilutions of A2MC2-infected MARC-145 cell culture supernatant reduced the number of NDV-GFP-positive cells (FIG. 1A), which indicated that the NDV replication was inhibited. This result indicated the existence of type I IFNs in the culture supernatant of the A2MC2-infected cells.

To further confirm that the antiviral activity was due to interferons, Western blot analysis was conducted to assess the protein levels of interferon-stimulated gene 56 (ISG56) and STAT2, in Vero cells. Blotting results showed that both ISG56 and STAT2 were elevated after treatment with the cell culture supernatant from A2MC2-infected MARC-145 cells (FIG. 1B). The levels of the proteins were similar to those of cells treated with 1000 U/ml IFN-α. These results indicate that A2MC2 induced synthesis of type I IFNs in MARC-145 cells.

PRRSV is known to inhibit production of type I IFNs. To confirm that A2MC2 is a genuine PRRSV isolate, an inhibition assay was performed by using antisense peptide-conjugated phosphorodiamidate morpholino oligomer (PPMO), 5UP 1, which inhibits replication of PRRSV in MARC-145 cells in a sequence-specific manner. A scrambled control PPMO CP1 was included as a negative control. An indirect immunofluorescence assay showed that 5UP1 blocked A2MC2 replication in MARC-145 cells (FIG. 1C), while CP1 had no effect. The lysate of A2MC2-infected MARC-145 cells was used for Western blot analysis with pig antiserum against PRRSV. Lysate samples of VR-2385- and MLV-infected cells were included as controls. Blotting results showed that A2MC2-infected cells had a band profile similar to MLV, though the bands were at a weaker intensity (FIG. 1D). The difference in band pattern between VR-2385 and MLV is likely because there is a deletion in nsp2 of VR-2385. These results confirmed that A2MC2 was a strain of PRRSV. Genotyping of this isolate was then performed.

Genotyping of PRRSV A2MC2 Strain

Figure 2:
FIG. 2. Illustration of sequence variation of A2MC2 in comparison to VR-2332 and MLV. The top line indicates the genomic sequence of VR-2332 and the numbers above the line indicate nucleotide positions in the genome. The nucleotide variations of MLV in comparison with VR-2332 are indicated by narrow vertical bars. The nucleotide variations of A2MC2 in comparison with VR-2332 are indicated by both narrow and wide vertical bars, among which the narrow vertical bars indicate that the nucleotides are the same as MLV and the wide bars indicate they are unique for A2MC2.

RT-PCR was conducted for the whole A2MC2 RNA genome. Sequencing of the cDNA was done and sequence analysis showed that it closely resembles Ingelvac PRRS MLV (GenBank ID: AF066183) and VR-2332 (GenBank ID: U87392), strains of genotype 2 PRRSV, at identity of 99.8%. There were a total of 28 nucleotide (nt) variations when compared to VR-2332, resulting in 14 amino acid changes (Table 1). The nucleotide variations were scattered from nt 4681 to the end of the genome (FIG. 2). The first 4680 nucleotides are identical to VR-2332. There were a total of 34 nucleotide variations when compared to strain MLV, resulting in 19 different amino acids. Compared to both VR-2332 and MLV, A2MC2 has 15 unique nucleotides scattered from nt 4681 to the end of the genome (FIG. 2). Ten of the unique changes occurred between nt 4681 and nt 10037 of the A2MC2 genome. The sequence from nt 11667 to 14420 of A2MC2 is the same as VR-2332 except 4 unique nucleotide variations. The sequence from nt 14421 to the end of the A2MC2 genome is the same as MLV except 1 unique nucleotide variation.

At the amino acid level, the A2MC2 differences when compared to VR-2332 were located in nsp3, nsp7, nsp8, nsp10, nsp11, nsp12, GP3, and M; and the variations from MLV sequence were located in nsp1β, nsp2, nsp8, nsp10, nsp11, nsp12, GP2, GP3, GP5, and M. Six unique amino acid changes occurred in A2MC2 when compared to VR-2332 and MLV: threonine to serine in nsp8, serine to alanine and proline to leucine in nsp10, serine to glycine in nsp12, methionine to valine, and isoleucine to valine in GP3 (Table 1). Nsp10 is a RNA helicase that unwinds dsRNA, while the functions of nsp8 and nsp12 are unknown. GP3 is a glycoprotein found in PRRSV virions as a minor structural component. The genomic sequence of A2MC2 when compared to both that of VR-2332 and MLV indicated that A2MC2 was possibly a chimera derived from these two strains.

Growth Properties of A2MC2 in MARC-145 and PAM Cells

Figure 3:
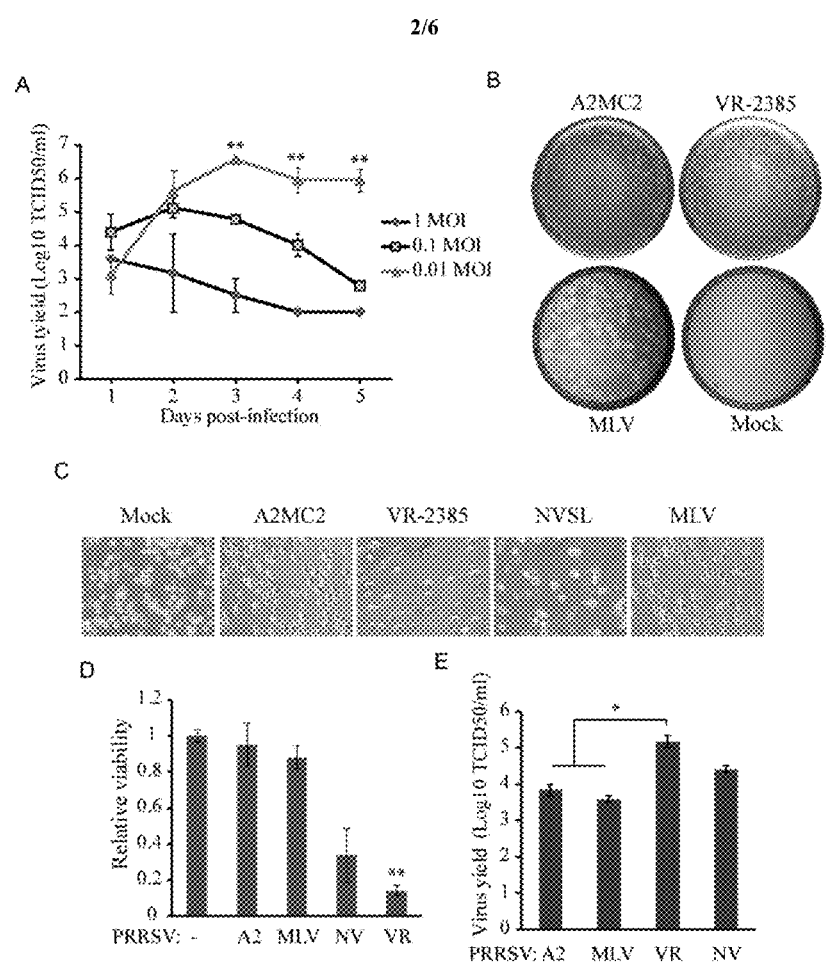

To determine the growth properties of A2MC2 in MARC-145 cells, a multi-step growth curve analysis was conducted. The cells were inoculated at a MOI of 0.01, 0.1 and 1 $TCID_{50}$ per cell, respectively. Cell culture supernatant samples were collected daily for five days after the inoculation and titrated for virus yield. The cells inoculated with 0.01 $TCID_{50}$ per cell had the highest virus yield, $10^{6.67}$ $TCID_{50}$ per ml on day 3, while the cells inoculated with 1 $TCID_{50}$ per cell had the lowest yield, lower than $10^3$ (FIG. 3A). The virus yields of cells with 0.01 $TCID_{50}$ increased from $10^3$ on day 1 to $10^{6.67}$ on day 3, and remained at $10^6$ on day 5. The virus yield of cells with 1 $TCID_{50}$ per cell decreased from $10^{3.5}$ on day 1 to $10^{2.5}$ on day 5. The virus yields of cells with 0.01 $TCID_{50}$ on day 3, 4 and 5 were significantly higher than those from cells with 0.01 and 1 $TCID_{50}$.

To further characterize the growth properties of A2MC2, plaque assays were conducted in comparison with VR-2385 and MLV strains. MARC-145 cells were inoculated with A2MC2, VR-2385, and MLV, respectively. Plaques were observed on 4 dpi after neutral red staining. The A2MC2-infected cells resulted in a small plaque morphology at around less than 1 mm in diameter, similar to VR-2385, while cells infected with MLV revealed a plaque morphology at around 5 mm in diameter, which was at least 5 times larger than those of A2MC2 (FIG. 3B). This result indicated that A2MC2 replication in MARC-145 cells was different from that of MLV.

To test if A2MC2 caused cytopathic effects (CPE) after infection of PAM cells, as it does in MARC-145 cells, we inoculated primary PAMs with PRRSV at a MOI of 0.05 $TCID_{50}$ per cell and observed the cells at 20 hpi under bright field microscopy. A2MC2 infection of PAMs caused no observable CPE, while VR-2385 and NVSL led to cell death (FIG. 3C). A2MC2-infected cells appeared similar to MLV-infected or uninfected PAM cells in morphology. A cell viability assay was conducted to assess the relative viability level between treatments. A2MC2-infected PAM cells showed a similar viability rate as was seen in uninfected cells, as did MLV infection, while VR-2385 significantly reduced viability to 0.14-fold (FIG. 3D). This result was consistent with the CPE observed under bright field microscopy.

Figure 4:
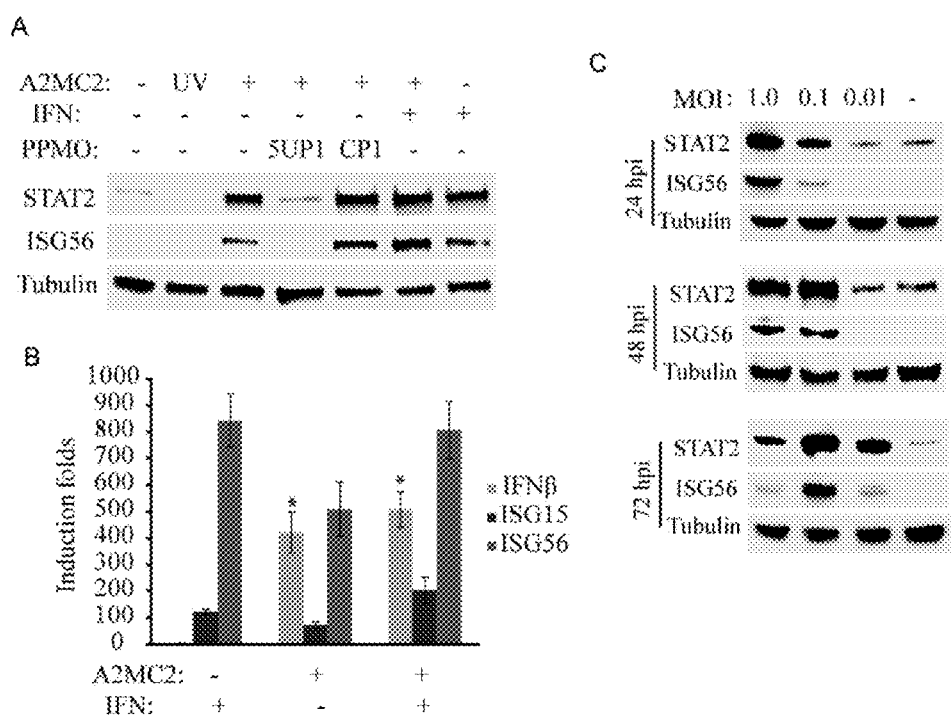
FIG. 4. A2MC2 replication induces elevated expression of IFN-stimulated genes in MARC-145 cells. A. Elevation of STAT2 and ISG56 detected by Western blotting. The cells were infected with A2MC2 or UV-inactivated virus at 1 MOI, followed by treatment with PPMO 5UP1 to inhibit A2MC2 replication, and at 24 hpi, treated with or without IFN-α. Cell lysate from uninfected cells was included as a control. B. Elevation of IFN-β, ISG15 and ISG56 expression detected by real-time PCR. Treatment of the cells with IFN-α was included as a control. Relative induction in comparison with mock-treated cells are shown. Error bars represent variation between repeated experiments. Significant differences between A2MC2-infected cells and the uninfected cells are denoted by "*", which indicate a P value of <0.05. C. Kinetics of STAT2 and ISG56 expression in MARC-145 cells infected with different MOIs of A2MC2. The cells were harvested at 24, 48 and 72 hpi for Western blot analyses. Samples of uninfected cell lysates were included as controls.

To determine virus yield in PAMs, cell culture supernatant was collected at 24 hpi and titrated in MARC-145 cells by IFA. The virus yields of A2MC2, MLV, VR-2385, and NVSL were $10^{3.8}$, $10^{3.6}$, $10^{5.2}$, and $10^{4.4}$ $TCID_{50}$ per ml, respectively (FIG. 3E). The results showed that viral yields of A2MC2 and MLV were significantly lower than VR-2385 ($P<0.05$), but did not vary much from the viral yield of NVSL. A2MC2 replication induces strong expression of STAT2 and ISG56 in MARC-145 cells To determine if A2MC2 replication induces IFN-stimulated genes in MARC-145 cells, the cells were infected with the virus at 1 $TCID_{50}$ per cell and harvested at 24 h post-infection (hpi). Western blot analysis showed that the levels of STAT2 and ISG56 in MARC-145 cells were remarkably elevated after A2MC2 infection (FIG. 4A). Treatment of A2MC2-infected cells with PPMO 5UP1 abolished the elevation, which indicated that the inhibition of A2MC2 removed the stimulation. UV-inactivated A2MC2 failed to induce the elevation of these two proteins, indicating that the elevation was A2MC2 replication-dependent.

Real-time RT-PCR was conducted to detect the transcripts of IFN-β, ISG15, and ISG56 in MARC-145 cells. Compared to mock-treated control wells, A2MC2 infection at 1 $TCID_{50}$ per cell induced 422-, 73-, and 509-fold RNA elevations of IFN-β, ISG15, and ISG56, respectively (FIG. 4B). The IFN-β transcript in A2MC2-infected cells was 105-fold higher than that of IFN-α-treated PRRSV-negative cells. The average levels of ISG15 and ISG56 transcripts in A2MC2-infected cells without external IFN-α were 1.68- and 1.6-fold, respectively, lower than those in IFN-α-treated PRRSV-negative cells. The differences of ISG15 and ISG56 between A2MC2 and uninfected cells were statistically insignificant. Addition of IFN-α to A2MC2-infected cells did not lead to a significant increase in expression of these three genes, compared to A2MC2-infected cells without external IFN-α.

As different MOI led to variable virus yields in MARC-145 cells, the protein levels of STAT2 and ISG56 in the cells after infection with different MOIs were assessed. Western blotting showed that the greater the MOI that was used to infect MARC-145 cells, the higher the level of STAT2 and ISG56 at 24 hpi detected (FIG. 4C). By 48 hpi, the cells with 0.1 $TCID_{50}$ had similar levels of these two proteins to 1 $TCID_{50}$. By 72 hpi, the cells with 1 $TCID_{50}$ had the lowest level of these two proteins. The results indicated that the high MOI inoculum was able to induce early synthesis of the two proteins, while a low MOI led to delayed induction.

Comparison with Other PRRSV Strains on IFN Production in MARC-145 Cells

To compare A2MC2 with other PRRSV strains in regards to IFN induction, MARC-145 cells were inoculated with A2MC2, VR-2385, NVSL, MLV, and VR-2332 at 1 TCID$_{50}$ per cell, separately. These strains were selected in part because VR-2385, VR-2332, and NVSL are PRRSV strains of varying virulence in experimentally infected pigs, and Ingelvac PRRS MLV is a licensed modified live vaccine strain. Cell culture supernatant samples were collected at 24 hpi and used to treat Vero cells for the IFN bioassay. Supernatants from A2MC2-infected cells inhibited NDV-GFP replication in Vero cells, while supernatant samples from MARC-145 cells infected with VR-2385, VR-2332, NVSL or MLV had no effect on NDV-GFP propagation in Vero cells (FIG. 5A).

Figure 5:
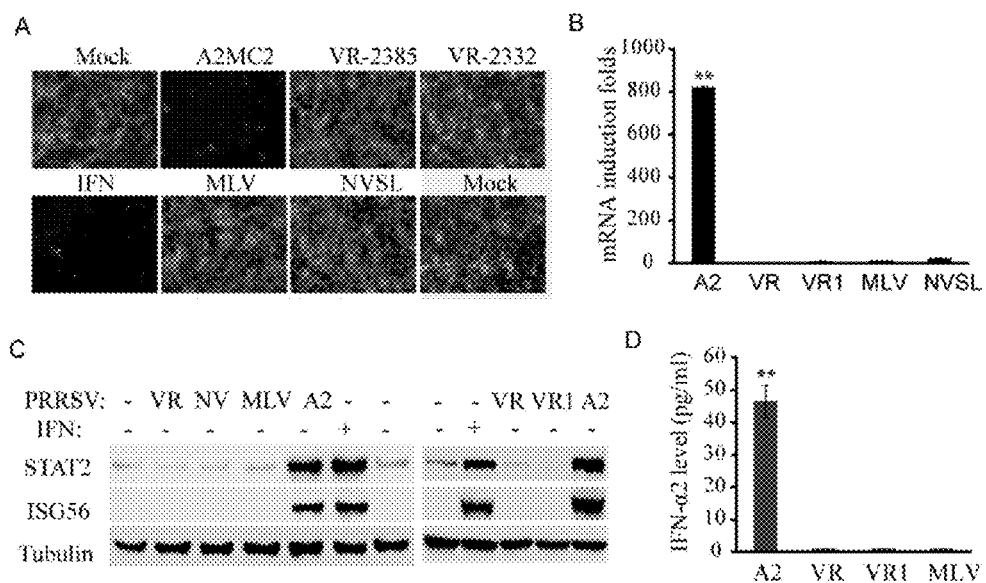
FIG. 5. Comparison of A2MC2 to other PRRSV strains in IFN production using MARC-145 cells. A. IFN bioassay in Vero cells. Cell culture supernatants from MARC-145 cells infected with 1 MOI each of PRRSV strains A2MC2, VR-2385, VR-2332, MLV, or NVSL, respectively, were collected at 36 hpi. Vero cells were treated with 1:4 dilution of the respective supernatants for 12 h, and then infected with NDV-GFP. Fluorescence microscopy was conducted at 24 hpi. Treatment with IFN-α was included as a positive control. B. IFN-β expression in MARC-145 cells detected by real-time PCR. The cells were infected with PRRSV and harvested for detection of IFN-β transcripts. Relative fold induction in comparison with uninfected cells are shown. Error bars represent variation between repeated experiments. The significant difference between A2MC2 and the rest of the samples is denoted by "", which indicate P<0.01. A2: A2MC2; VR: VR-2385; VR1: VR-2332. C. STAT2 and ISG56 protein level in MARC-145 cells detected by Western blotting. Treatment of uninfected cells with IFN-α was included as a positive control. A2: A2MC2; VR: VR-2385; NV: NVSL; VR1: VR-2332. D. IFN-α2 level in culture supernatants of MARC-145 cells infected with A2MC2, VR-2385, VR-2332, and MLV, respectively. ELISA analyses were conducted to quantify the IFN-α2 levels, and concentrations were calculated on the basis of a standard curve. The significant difference between A2MC2 and the rest of the samples is denoted by "", which indicate P<0.01.

Real-time RT-PCR analysis showed that A2MC2 induced an 820-fold elevation of IFN-β transcripts in MARC-145 cells, significantly higher than that induced by VR-2385, VR-2332, NVSL, or MLV (FIG. 5B). Western blot analysis showed that VR-2385, VR-2332, NVSL, and MLV infection had no effect on STAT2 and ISG56 protein level, while A2MC2 infection led to a higher amount of the two proteins (FIG. 5C).

ELISA was done to detect IFN level in culture supernatants of MARC-145 cells infected with A2MC2, VR-2385, VR-2332, or MLV, respectively. Due to paucity of ELISA kits for type I IFNs of monkeys, only the level of monkey IFN-α2 was quantified. The level of IFN-α2 in culture supernatant of A2MC2-infected cells was 46.6 pg/ml and significantly higher than the supernatants of MARC-145 cells infected with VR-2385, VR-2332 or MLV (FIG. 5D). These results indicated that A2MC2 induced synthesis of type I IFNs in MARC-145 cells, while the other four PRRSV strains inhibited IFN induction.

Kinetics of IFN-β Expression in A2MC2-infected MARC-145 Cells

Figure 6:
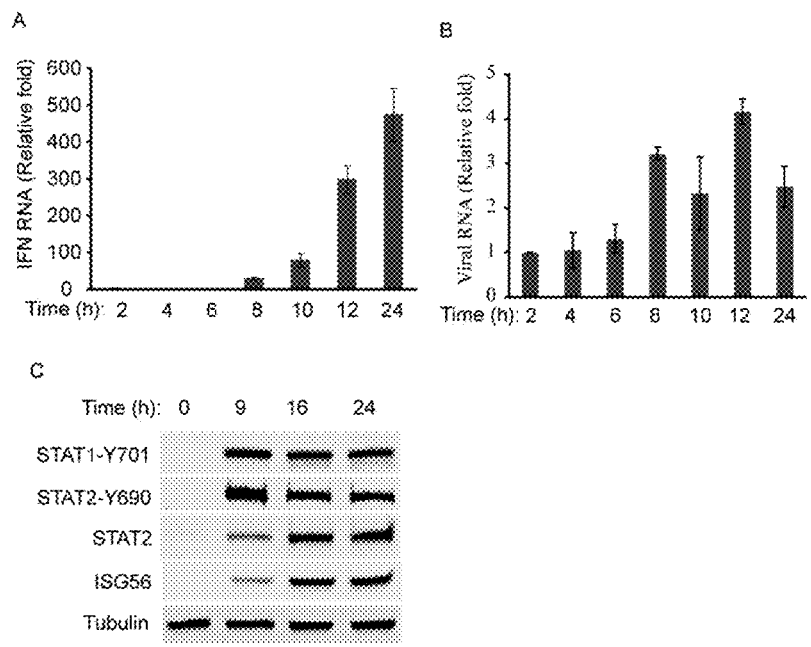
FIG. 6. Time-course kinetics of IFN-β expression and activation of the JAK-STAT signaling pathway in A2MC2-infected MARC-145 cells. A. Time-course kinetics of IFN-β expression. The cells were infected with A2MC2 at 1 MOI and harvested at 2, 4, 6, 8, 10, 12, and 24 hpi for real-time PCR detection of IFN-β transcripts. Relative fold of induction in comparison with uninfected cells are shown. Error bars represent variation between repeated experiments. B. Viral RNA levels detected by real-time RT-PCR. Relative fold of viral RNA in comparison with that detected at 2 hpi are shown. C. Activation of the JAK-STAT signaling pathway. The cells were infected with A2MC2 at a MOI of 1 and harvested at 0, 9, 16, and 24 hpi for Western blot analysis of phosphorylated STAT1 (STAT1-Y701) and STAT2 (STAT2-Y690), whole STAT2, and ISG56.

To further examine the expression of IFN-β in A2MC2-infected MARC-145 cells, the cells were harvested at 2, 4, 6, 8, 10, 12, and 24 hpi for RNA isolation and real-time RT-PCR. The IFN-β mRNA increased from 2-fold at 2 hpi to 474-fold at 24 hpi (FIG. 6A). The large increase of IFN-β transcripts started at 8 hpi. This result indicates that IFN-β expression increased concurrently with A2MC2 replication. Viral RNAs at these time points were detected by real-time RT-PCR. The results showed that the viral RNAs detected at 8, 10, 12 and 24 hpi were 3.2-, 2.3-, 4.2-, and 2.5-fold, respectively, higher than 2 hpi (FIG. 6B). The relatively small increase in the viral RNA level is consistent with the result of the multi-step growth curve showing limited virus replication in cells inoculated with 1 TCID$_{50}$ per cell.

The data above showed that A2MC2 induced expression of type I IFNs. We were interested in the status of JAK-STAT signaling pathway in A2MC2-infected cells. STAT1 and STAT2 proteins are key players in JAK/STAT signaling, a pathway activated by type I IFNs. Phosphorylation of STAT1 and STAT2 is an early step in the pathway after IFNs bind to their receptors. To determine if A2MC2-induced IFNs resulted in the activation of these two proteins, we tested the phosphorylation status of STAT1 and STAT2 in MARC-145 cells at 0, 9, 16 and 24 hpi. The selection of 9 hpi was based on the speculation that after increase of IFN-β transcript at 8 hpi, phosphorylation of STAT1 and STAT2 would be detected. The inclusion of 16 and 24 hpi was based on the speculation that along with the increase of IFN-β expression, phosphorylation of STAT1 and STAT2 would continue. The result showed that the levels of phosphorylated STAT1 at tyrosine 701 (STAT1-Y701) and STAT2 at tyrosine 690 (STAT2-Y690) were greatly increased at 9 hpi (FIG. 6C), indicating A2MC2-induced IFNs led to the activation of STAT1 and STAT2. Moreover, the total STAT2 and ISG56 were detectable at 9 hpi and increased at 16 and 24 hpi (FIG. 6C). This result suggested that A2MC2-induced IFNs resulted in the activation of JAK-STAT signaling, which then led to the increased expression of STAT2 and ISG56.

Figure 7:
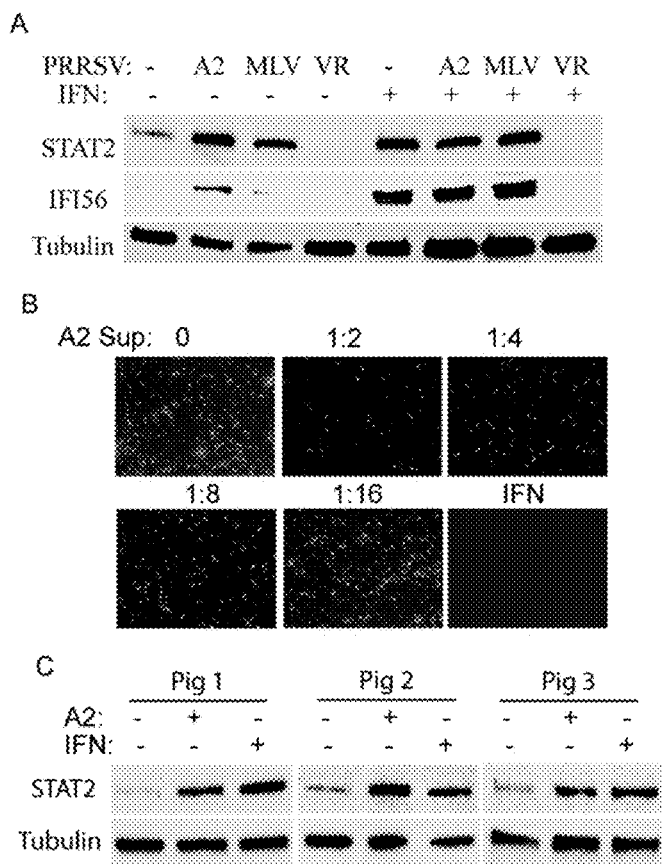
FIG. 7. A2MC2 induces expression of IFN-stimulated genes in primary porcine pulmonary alveolar macrophages (PAMs). A. STAT2 and IF156 detected by Western blotting. PAMs were infected with PRRSV strains VR-2385, A2MC2, and MLV, and at 12 hpi, treated with or without IFN-α. The cells were harvested at 20 hpi for Western blotting. Cell lysate samples from uninfected PAMs with or without IFN treatment were included as controls. B. IFN bioassay in CRL2843 cells. Supernatant from A2MC2-infected PAMs was diluted and added to the CRL2843 cells 12 h before NDV-GFP inoculation. The cells were observed 24 h after NDV-GFP inoculation. Treatment of the cells with swine IFN-α at a final concentration of 1000 U/ml was included as a positive control. C. A2MC2 induces elevation of STAT2 in PAM cells from different piglets. PAMs from three piglets were inoculated with A2MC2 at 0.05 MOI, respectively, and incubated for 20 h. Cell lysate samples from IFN-α-treated PAM cells were included as positive controls. Cell lysate samples from non-infected cells were included as negative controls in the Western blotting analyses.

A2MC2 Induces Elevated Expression of ISGs in Primary Porcine Alveolar Macrophages PAMs are the main target cells for PRRSV infection in vivo. To determine the effect of A2MC2 on IFN synthesis in PAM cells, PAMs were infected with A2MC2 and harvested for Western blot analyses at 20 hpi. Infections of PAMs with VR-2385 and MLV were included as controls. Compared to uninfected cells, A2MC2 infection resulted in the elevation of STAT2 and IFI56 (equivalent to ISG56 in primates), while VR-2385 led to no change of these two proteins, and MLV led to a slight elevation of STAT2 (FIG. 7A). To test the effect of these virus strains on IFN signaling, IFN-α was added to PAMs at 12 hpi. PAMs infected with A2MC2 and MLV had elevated STAT2 and IFI56 to a similar level of uninfected cells treated with external IFN-α, while VR-2385-infected cells had no change in STAT2 and IFI56 levels (FIG. 7A). This result indicated that A2MC2 and MLV had an undetectable effect on IFN downstream signaling while VR-2385 inhibited the IFN activation in PAMs.

The IFN bioassay was conducted to assess IFNs in culture supernatant of A2MC2-infected PAMs. CRL2843 cells are immortalized porcine alveolar macrophages that are not susceptible to PRRSV infection. The cells were treated with dilutions of the supernatant from A2MC2-infected PAMs and, on the next day, inoculated with NDV-GFP. The supernatant dilutions up to 1:8 inhibited NDV-GFP replication, compared with mock-infected cells (FIG. 7B). This result indicated that the culture supernatant of A2MC2-infected PAMs contained interferons.

To determine if the induction of IFNs by A2MC2 is not limited to PAMs from one piglet, PAMs from three other piglets were inoculated with A2MC2 and incubated for 20 h. Western blot analysis showed that A2MC2 infection induced the elevation of STAT2 in PAM cells from all three other piglets (FIG. 7C). The level of STAT2 in A2MC2-infected PAMs was similar to that in PAMs treated with external IFN-α.

It will be apparent from the foregoing that embodiments of the invention induce the synthesis of type I interferons in MARC-145 and primary PAM cells. The experiments presented describe analysis of the induction of IFNs by A2MC2 from several aspects. First, the culture supernatant from A2MC2-infected MARC-145 cells protected Vero cells from NDV infection. Vero cells are defective in IFN production and not susceptible to PRRSV. Pretreatment of the cells with dilutions of A2MC2-derived supernatant induced an antiviral response in Vero cells that inhibited the replication of NDV. The result was corroborated by elevation of STAT2 and ISG56, two genes stimulated by IFN signaling in Vero cells. Second, the elevated expression of STAT2 and ISG56 was shown in A2MC2-infected MARC-145 cells. Virus replication was essential for the elevation of the two proteins because UV-inactivated virus and PPMO inhibition of PRRSV replication did not lead to elevation of these host proteins. The results indicate that viral replication in the cytoplasm stimulated PRRs, leading to IFN synthesis. The elevation of the transcripts of ISG15 and ISG56 further confirmed the observation. This result also ruled out the possibility of contamination by other swine pathogens because PPMO-mediated inhibition of A2MC2 led to an absence of IFN induction. Other common swine pathogens, such as porcine respiratory coronavirus (PRCV) or swine influenza virus (SwIV), can induce synthesis of a high level bioactive IFN-α. Interestingly, A2MC2 infection at different MOIs induced variable levels of ISG expression. The higher the MOI, the earlier A2MC2 induced ISG elevation. The lower the MOI, the later the virus-induced ISG expression and the lower level of induction. This result provided an explanation as to why a MOI of 1 $TCID_{50}$ per cell led to a lower virus yield than MOIs of 0.1 and 0.01 $TCID_{50}$. It indicates that the inoculum of 0.01 $TCID_{50}$ per cell resulted in limited initial virus replication, leading to a weaker stimulation on cellular PRRs, which allowed the virus to complete its replication cycles. On the other hand, the inoculum at 1 $TCID_{50}$ per cell stimulated a more robust response in regards to PRRs and IFN synthesis, which in turn inhibited virus spread to neighboring cells or continued replication.

Third, several other PRRSV strains including the vaccine strain MLV were shown to inhibit IFN production. IFN-α2 was detected in culture supernatant from A2MC2-infected cells, but not in the samples from cells infected with VR-2332, VR-2385, or MLV. It was possible that there were other subtypes of type I IFNs in the supernatant from A2MC2-infected cells, as IFN-β mRNA level significantly increased. We further tested IFN production in A2MC2 infection of PAM cells. The STAT2 and IF156 were elevated in A2MC2-infected cells, but not in VR-2385-infected cells. The A2MC2 induction of IFNs was pig-independent as PAMs isolated from three other pigs had similar elevations of STAT2 after A2MC2 infection. Infection of PAMs with MLV also led to a slight elevation in STAT2 level, which indicates that MLV might induce STAT2 albeit at much lower levels than A2MC2.

Analysis of the cDNA sequence of the A2MC2 genome showed that it was highly homologous to both VR-2332 and MLV. This result indicated that A2MC2 might be a chimera of VR-2332 and MLV strains. Based on sequence analysis, we reasoned that the first 4.6 kb and the fragment from nt 11966 to 14420 were derived from VR-2332; fragments of nt 10697 to 11666 and nt 14421 to the end of the genome were possibly of MLV origin; and the fragment of nt 4681 to 10037 was derived from either one of them, but with mutations as 10 unique changes are located in this fragment. Compared to both VR-2332 and MLV, A2MC2 possessed 6 unique amino acids distributed in nsp8, nsp10, and nsp12, and GP3.

Both A2MC2 and MLV have an undetectable effect on the ability of IFN-α to induce an antiviral response, as their infection of PAM cells did not affect expression of STAT2 and IF156 activated by external IFN-α. This result is consistent with a previous report that virulent strain VR-2385 inhibits IFN signaling while MLV does not. The plaque morphology of A2MC2 was much smaller than that of MLV, which indicated that MLV replicated with faster kinetics than A2MC2 in MARC-145 cells. In addition, A2MC2 infection did not lead to any observable cytopathic effect in PAM cells, and A2MC2-infected cells were of similar viability as mock-infected or MLV-infected cells. These features indicated that like MLV, A2MC2 might be less suitable to replicate in PAMs.

We tested if A2MC2 replication led to IRF-3 phosphorylation using polyinosinic-polycytidylic acid (poly(I:C)), a synthetic analog of double-stranded RNA (dsRNA), as a positive control. The phosphorylated IRF-3 was detected in the poly(I:C)-treated cells but undetectable in cells infected with A2MC2 (data not shown). The result that A2MC2 infection led to increase of IFN-β transcript from 8 hpi to less than 1000-fold at 24 hpi (FIG. 6) indicated that A2MC2 replication might lead to a low level of IRF-3 signaling for an extended period.

Thus, the present invention discloses in part the discovery and isolation of a strain of PRRSV, A2MC2, that induced IFN production in both MARC-145 and PAM cells while other tested PRRSV strains inhibited IFN induction. Specifically, A2MC2 induced type I IFNs and led to an elevation of IFN-stimulated genes. Based on these promising attributes of the virus, we conducted the in vivo studies which are described in Example 2.

The following materials and methods were used to produce the results described in this Example.

Cells and Viruses

MARC-145 and Vero cells (ATCC CCL-81) were grown in Dulbecco's Modified Eagle's Medium (DMEM) supplemented with 10% fetal bovine serum (FBS). Immortalized porcine macrophages (CRL2843) were cultured in RPMI1640 medium supplemented with 10% FBS. Primary PAM cells were prepared from bronchoalveolar lavage of 4-week-old PRRSV-negative piglets. The preparation and subsequent culture of PAMs in RPMI1640 culture medium were conducted, as previously described. PRRSV strains A2MC2, VR-2385, NVSL 97-7895, and Ingelvac PRRS MLV were used to inoculate MARC-145 cells at 1 multiplicity of infection (MOI). Virus titers were determined in MARC-145 cells for the median tissue culture infectious dose ($TCID_{50}$), as previously described. Avirulent LaSota Newcastle disease virus carrying the gene of green fluorescence protein (NDV-GFP) was propagated in Vero cells, as previously described.

Virus inactivation was conducted with a UV cross-linker (Spectrolinker XL-1500, Agilent Technologies, Santa Clara, Calif.) at 1200 $mJ/cm^2$ for two 10-min pulses at 1-min interval. The inactivation was confirmed by the absence of virus replication in MARC-145 cells at 72 h post-infection (hpi) as assessed by immunofluorescence assay (IFA).

For interferon stimulation, universal type I IFN-α (R&D Systems, Minneapolis, Minn.) was added to the cultured cells at a final concentration of 1000 U/ml. The cells were harvested at indicated time points for further analysis.

Interferon Bioassay

Vero cells were seeded into cell culture plates, incubated overnight, and, on the next day, treated with culture supernatant from PRRSV-infected MARC-145 cells. The cells were infected with LaSota NDV-GFP 12 h after the treatment. Fluorescence microscopy was conducted 24 h after infection to observe GFP-positive cells.

Immunofluorescence Assay (IFA)

An IFA was carried out as previously reported with an N-specific monoclonal antibody EF11 to detect PRRSV N proteins in MARC-145 cells on coverglass slips. Specific reactions between EF11 and the N protein were detected with goat anti-mouse IgG-fluorescein isothiocyanate (FITC) conjugate (Sigma, St. Louis, Mo.). The coverglass was mounted onto slides using SlowFade Gold antifade reagent containing 4'6-diamidino-2-phenylindole (DAPI) (Life Technologies Corporation, Carlsbad, Calif.) and observed under fluorescent microscopy.

Western Blot Analysis

Cell lysate samples were analyzed by sodium dodecyl sulfate-polyacrylamide gel electrophoresis (SDS-PAGE) and Western blot analysis as described previously. Briefly, separated proteins from SDS-PAGE were transferred onto a nitrocellulose membrane and probed with antibodies against STAT2 (Santa Cruz Biotechnology, Santa Cruz, Calif.), β-tubulin (Sigma), phospho-STAT2 (STAT2-Y690) (Santa Cruz Biotechnology), phospho-STAT1 (STAT1-Y701) (Millipore, Billerica, Mass.), and ISG56 (Thermo Fisher Scientific, Rockford, Ill.). The chemiluminescent signal was recorded digitally by Quantity One Program, Version 4.6, in a Chemi-Doc XRS imaging system (Bio-Rad Laboratories, Hercules, Calif.). Pig antiserum against PRRSV NVSL strain (NVSL, Ames, Iowa) was used to detect PRRSV proteins in lysate of PRRSV-infected cells (Patel et al., 2010).

RNA Isolation, Reverse Transcription, and Real-Time PCR

Total RNA was isolated from MARC-145 and PAM cells with TRIzol® Reagent (Life Technologies) following the manufacturer's instructions. Reverse transcription and real-time PCR were conducted as previously described. Transcripts of ribosomal protein L32 (RPL32) were also amplified from the samples of PAM and MARC-145 cells and used to normalize the total input RNA. Primers used in this study to conduct reverse transcription and real-time RT-PCR were previously described. Relative transcript levels were quantified by the $2^{-\Delta\Delta C_T}$ method and shown as a relative fold of change in comparison with mock-treated control.

Cell Viability Assay

Viability of PAMs was determined with CellTiter-Glo Cell Viability Assay (Promega). Briefly, CellTiter-Glo reagent was added to cells in a 96-well plate and the luminescence signal was measured with VICTOR3™ Multilabel Counter (Perkin-Elmer Life and Analytical Sciences, Wellesley, Mass.). Relative percentages of luminescence intensity were calculated by comparison to controls.

Plaque Assay

Plaque assays were done with modifications from a previously described protocol. MARC-145 cells were seeded into 35 mm culture dishes and incubated overnight. PRRSV was diluted in a ten-fold series and added to the cells. The virus inoculum was removed 2 h after inoculation and replaced with 0.5% agarose overlay containing complete growth medium. The cells were stained with another layer of agarose overlay containing neutral red at 50 µg/ml 4 days after inoculation. Plaques were observed after overnight incubation.

Quantifying IFN Level by ELISA

Culture supernatant samples of MARC-145 cells infected with A2MC2, VR-2385, VR-2332, or MLV at a MOI of 1 TCID$_{50}$ per cell were collected at 24 hpi. Detection of IFN-α2 in each sample was done by using VeriKine™ Cynomolgus/Rhesus Interferon-Alpha Serum ELISA kit (PBL Interferon-Source, Piscataway, N.J.) according to the manufacturer's instruction. The concentration of IFN-α2 in the samples was calculated on the basis of a standard curve prepared from supplied IFN-α2 in the kit.

Sequencing

A2MC2 genomic RNA was isolated from cell culture supernatant with TRIzol LS reagent (Life Technologies). Reverse transcription of the viral RNA with primers 32nsp12R1 (5'-TCAATTCAGGCCTAAAGTTG-3'-SEQ ID NO:17) and P6-7-R (5'-CGCCCTAATTGAATAGGT-GACTT-3'-SEQ ID NO:18) was done with Maxima reverse transcriptase (Thermo Fisher Scientific). PCR amplification was done with Phusion high-fidelity DNA polymerase (New England Biolab, Ipswich, Mass.). 5'-RACE (rapid amplification of cDNA ends) and 3'-RACE of the A2MC2 genome were done as previously described. Sequencing of the PCR products was performed with ABI Prism 3130 Genetic Analyzer (Life Technologies). Sequence assembly and analysis was done with LaserGene Core Suite (DNASTAR Inc., Madison, Wis.). The GenBank accession number of the cDNA sequence of the A2MC2 genome is JQ087873.

Statistical Analysis

Differences in indicators between treatment samples, such as cellular RNA level between the groups in the presence or absence of PRRSV infection, were assessed by the Student t-test. A two-tailed P-value of less than 0.05 was considered significant.

TABLE 1

Nucleotide variations in A2MC2 sequence leading to unique amino acid changes compared with both MLV and VR-2332[a]

| | Nucleotide[c] | | | Amino acid[d] | | | | |
|---|---|---|---|---|---|---|---|---|
| Position[b] | A2MC2 | MLV | VR-2332 | A2MC2 | MLV | VR-2332 | Protein[e] | Position (aa)[f] |
| 7621 | T | A | A | S | T | T | nsp8 | 20 |
| 9627 | G | T | T | A | S | S | nsp10 | 4 |
| 9655 | T | C | C | L | P | P | nsp10 | 13 |
| 12012 | G | A | A | G | S | S | nsp12 | 135 |
| 12972 | G | A | A | V | M | M | GP3 | 93 |
| 12975 | G | A | A | V | I | I | GP3 | 94 |

[a]GenBank accesssion numbers: VR-2332 (GenBank ID: U87392), MLV (GenBank ID: AF066183), and A2MC2 (GenBank ID: JQ087873).
[b]Nucleotide positions are indicated on left column based on VR-2332 sequence.
[c]Nucleotides at the indicated positions are listed.
[d]Amino acids derived from the codon of indicated nucleotides are listed.
[e]Proteins corresponding to the amino acids derived from the codon of indicated nucleotide positions are listed on the right column.
[f]Position of an amino acid (aa) in the target protein.

EXAMPLE 2

This Example demonstrates use of compositions of the invention for stimulating immune responses against PRRSV in pigs.

Pig inoculation. Three-week-old PRRSV-negative piglets were randomly divided into 9 groups (Table 2). The pigs were inoculated via intramuscular (I.M.) or intranasal (I.N.) routes with the PRRSV isolate. The two routes of inoculation were used to mimic natural infection (I.N.) and vaccine delivery (I.M.). PRRSV A2MC2 (an interferon-inducing strain), VR-2385 (a moderate virulent strain) and MLV (a vaccine strain) were used in the pig inoculation. Contact controls of 2 piglets in each of group 1 to 7 were included to test PRRSV shedding and transmission. Phosphate-buffered saline (PBS) pH7.2 was used for mock-infected controls. The pigs were observed for two months.

TABLE 2

Pig test design

| Event | Group 1 | Group 2 | Group 3 | Group 4 | Group 5 | Group 6 | Group 7 | Group 8 | Group 9 | Total |
|---|---|---|---|---|---|---|---|---|---|---|
| PRRSV | A2MC2 | A2MC2 | VR2385 | VR2385 | MLV | MLV | pA2MC2 | PBS | PBS | |
| Dose (TCID50) | $10^5$ | $10^5$ | $10^5$ | $10^5$ | $10^5$ | $10^5$ | $10^5$ | N/A | N/A | |
| Routes | I.M. | I.N. | I.M. | I.N. | I.M. | I.N. | I.N. | I.M. | I.N. | |
| Number of Piglets | 4 | 8 | 4 | 8 | 4 | 8 | 8 | 4 | 8 | 56 |
| Contact control | 2 | 2 | 2 | 2 | 2 | 2 | 2 | 0 | 0 | 14 |
| Necropsy at 14 dpi | 0 | 4 | 5 | 4 | 0 | 4 | 4 | 0 | 4 | |

Blood samples for serum were collected once a week. Serum was separated and stored at −80° C. freezer for subsequent determination of levels of viral RNA and anti-PRRSV antibodies. The piglets were weighed before the start of the experiment and before necropsy.

To evaluate lung lesions, necropsies were performed on day 14 after infection for 4 piglets in group 2, 4, 6, 7 and 9. Blood was collected and tested for PRRSV RNA. Samples of lung and other tissues were collected during necropsy for histological examination, scoring and immunohistochemistry staining with PRRSV N-specific antibody. Evaluation of gross and microscopic lung lesions was done in a blinded fashion. All other pigs were subjected for necropsy at the end of the experiment. Whole blood samples were collected for lymphocyte isolation. Serum samples were collected for detection of neutralizing antibody and PRRSV RNA.

Viremia, Daily Weight Gain and Neutralizing Antibody

Figure 8:
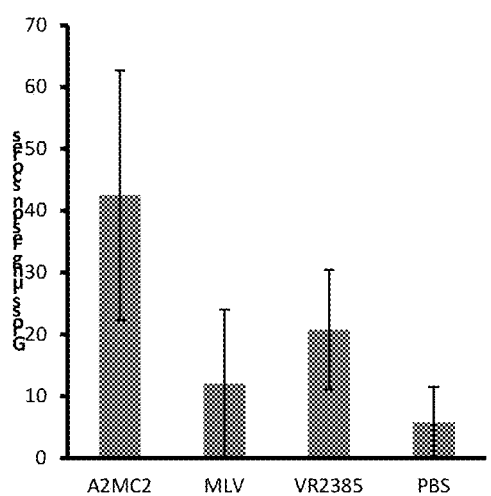
FIG. 8. Gross lung lesion in pigs at 14 days post-infection (dpi). Pigs were inoculated with PRRSV A2MC2, MLV or VR-2385. PBS was included as negative control. Four pigs from each group were necropsied at 14 dpi. Average gross lung lesion scores are shown. Error bar represents variation among the four pigs in each group.
Figure 9:
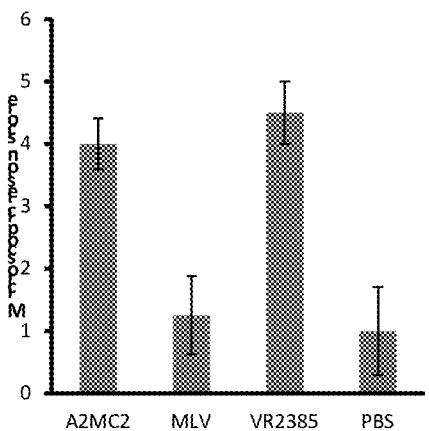
FIG. 9. Interstitial pneumonia in pigs at 14 dpi. Pigs were inoculated with PRRSV A2MC2, MLV or VR-2385. Four pigs from each group were necropsied at 14 dpi. Average scores of microscopic lesions are shown. Error bar represents variation among the four pigs in each group.

Lung lesions. During necropsy, lung was observed for gross pathology and scored. Sections of lung were assessed for interstitial pneumonia under microscopy. Among the A2MC2-infected pigs, three had lung pathology and one had no gross pathology. Among the MLV-infected pigs, only one had lung pathology. Among the VR-2385-infected pigs, three had lung pathology and one had no visible change. The average gross lung lesion scores show that A2MC2-infected pigs had higher scores than the other groups (FIG. 8). Under microscopy, the interstitial pneumonia in A2MC2-infected pigs was similar to VR-2385-infected pigs, both groups had higher scores than MLV-infected pigs (FIG. 9). These results indicate that A2MC2 has similar moderate virulence to VR-2385, while MLV is non-virulent.

Figure 10:
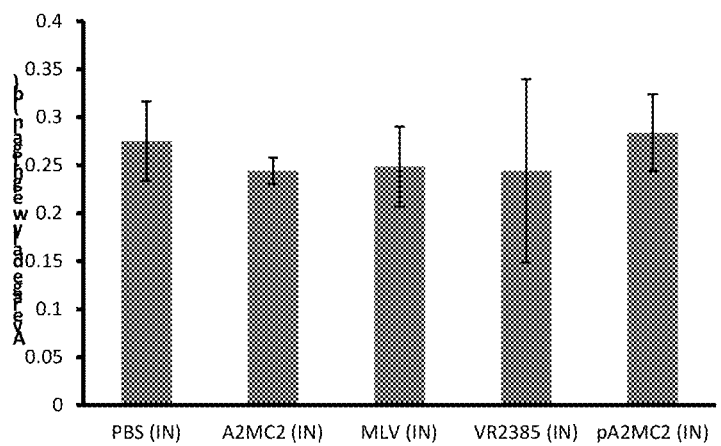
FIG. 10. Average daily weight gain. Pigs were inoculated with PRRSV A2MC2, MLV or VR-2385. PBS was included as negative control. Average daily weight gain during the course of the study is shown at week 2 (FIG. 10A) and week 8 (FIG. 10B). Error bar represents variation among the four pigs in each group.
Figure 10:
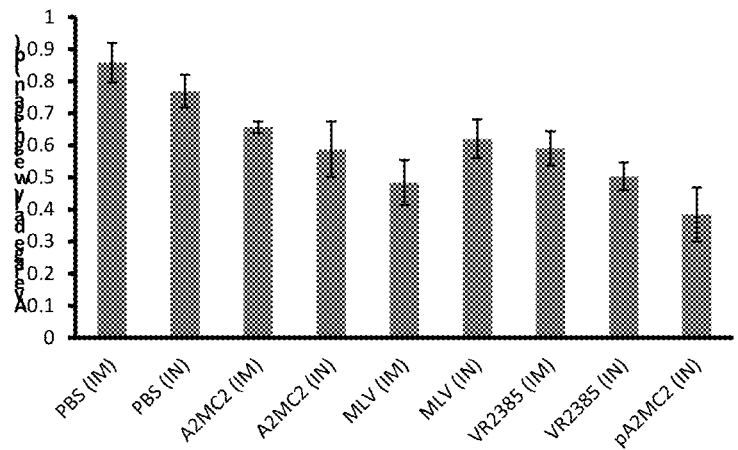

Average daily weight gain. The pigs were weighed on arrival and before necropsy. Average daily weight gain was calculated for each group. At week 2, all groups had similar average daily weight gain (FIG. 10A). At week 8, the PRRSV-inoculated pigs had slightly lower average daily weight gain than uninfected pigs (PBS groups) (FIG. 10B). The A2MC2- or VR-2385-infected pigs had similar weight gain to MLV-infected pigs. This result indicates that A2MC2 had no adverse effect on daily weight gain in comparison with MLV strain.

Detection of PRRSV replication. The blood samples collected weekly were used for detection of PRRSV RNA level in blood. The viral RNA level indicates the viral replication status. A part of the serum samples were mixed with TriZol LS (Invitrogen) for RNA isolation as instructed by the manufacturer. RNA was converted to cDNA using qScript cDNA Synthesis kit (Quanta Biosciences). Quantitative real-time PCR was performed to detect PRRSV genomic copies, as previously reported.

Analysis of serum samples of DPI 7 and 14 shows that pigs inoculated with A2MC2 and VR-2385 had similar level viremia, but pigs with MLV had much lower Viremia. No data is shown as this work is ongoing.

Neutralizing antibody titration. Neutralization assay was performed on MARC-145 cells, as described previously. Serum samples were tested for neutralizing antibodies against VR-2332. This assay is expected to show the time kinetics of neutralizing antibodies in the pigs, which may indicate protective immune response against PRRSV. It is expected that the pigs receiving this new strain would yield higher titer of neutralizing antibody and longer duration of the antibody than the other two strains.

Analysis shows that A2MC2 infection induced earlier and higher neutralizing antibody than MLV and VR-2385 (Table 3). Contact pigs of A2MC2 developed neutralizing antibody, but MLV and VR-2385 contact pigs had no or minimal level (Table 4). For A2MC2 and MLV, I.N. delivery induced more neutralizing antibody than I.M. route, but had minimal effect for VR-2385. Rescued virus from infectious clone pA2MC2 induced neutralizing antibody at similar level to parent strain though at a later onset. There is no apparent correlation between intestinal pneumonia development and neutralizing antibody generation.

TABLE 3

Number of pigs that had neutralizing antibody (serum dilution 1:10) against VR-2332 (4 pigs in each group)

| PRRSV | Inoculation route | Week 1 | Week 2 | Week 3 | Week 4 | Week 5 | Week 6 | Week 7 | Week 8 |
|---|---|---|---|---|---|---|---|---|---|
| A2MC2 | I.M. | 0 | 0 | 0 | 1 | 0 | 1 | 3 | 3 |
| | I.N. | 0 | 1 | 1 | 2 | 0 | 2 | 3 | 4 |
| MLV | I.M. | 0 | 0 | 0 | 0 | 0 | 0 | 0 | 1 |
| | I.N. | 0 | 0 | 0 | 0 | 1 | 1 | 2 | 4 |
| VR-2385 | I.M. | 0 | 0 | 0 | 0 | 0 | 0 | 2 | 1 |
| | I.N. | 0 | 0 | 0 | 1 | 0 | 0 | 1 | 1 |
| pA2MC2 | I.N. | 1 | 0 | 0 | 0 | 1 | 2 | 3 | 3 |
| Total | | 1 | 1 | 1 | 4 | 2 | 6 | 14 | 17 |

TABLE 4

Number of contact pigs that had neutralizing antibody (serum dilution 1:10) (2 pigs in each group)

| PRSSV | From route group | Week 1 | Week 2 | Week 3 | Week 4 | Week 5 | Week 6 | Week 7 | Week 8 |
|---|---|---|---|---|---|---|---|---|---|
| A2MC2 | I.M. | 0 | 0 | 1 | 0 | 2 | 1 | 2 | 1 |
|  | I.N. | 0 | 0 | 1 | 1 | 1 | 2 | 2 | 2 |
| MLV | I.M. | 0 | 0 | 0 | 0 | 0 | 0 | 0 | 0 |
|  | I.N. | 0 | 0 | 0 | 0 | 0 | 0 | 0 | 1 |
| VR-2385 | I.M. | 0 | 0 | 0 | 0 | 0 | 0 | 1 | 1 |
|  | I.N. | 0 | 0 | 0 | 0 | 0 | 0 | 1 | 0 |
| pA2MC2 | I.N. | 1 | 0 | 0 | 0 | 0 | 1 | 1 | 1 |
| Total |  | 1 | 0 | 2 | 1 | 3 | 4 | 7 | 6 |

Among the pigs infected with A2MC2 via I.N., one pig had neutralizing antibody by week 2 post infection. The onset of neutralizing antibody in the group of pigs infected with A2MC2 via I.M. was delayed to week 4. All A2MC2-infected pigs except one via I.M. developed neutralizing antibody by week 8. Among pigs infected with MLV via I.N., one pig had neutralizing antibody by week 5. The onset of neutralizing antibody in the group of pigs infected with MLV via I.M. was delayed to week 8. Only one pig had neutralizing antibody in MLV I.M. group (25%) by week 8, which is far less than A2MC2 I.M. group (75%). Among pigs infected with VR-2385, only one pig in I.N. or I.M. group had neutralizing antibody by week 8. The development of neutralizing antibody seems not correlating with Viremia, as MLV groups had lower Viremia than the other groups.

The neutralizing antibody in contact pigs had similar trend as inoculated pigs in Table 3. The pigs in contact groups of A2MC2 had neutralizing antibody by week 3. Only one pig in MLV contact group had neutralizing antibody.

PRRSV strains are known to be heterogeneous. The neutralization assay described above was done with VR-2332. So we also conducted neutralization assay with VR-2385 for serum samples on week 7 and week 8 post-infection. The result showed that those serum samples of week 7 were consistent in both assays with VR-2332 and VR-2385, but 6 more serum samples of week 8 (all were VR-2385-infected pigs) had neutralizing antibody. This indicates that the 6 pigs had strain-specific neutralizing antibody, while those induced by MLV or A2MC2 were able to neutralize both VR-2332 and VR-2385. In summary, A2MC2, the interferon-inducing strain, induces earlier and more neutralizing antibody than MLV and VR-2385.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

---

What is claimed is:

1. A composition comprising a polynucleotide, wherein the polynucleotide encodes at least one amino acid sequence selected from the group of amino acid sequences consisting of SEQ ID NO:1, SEQ ID NO:2, SEQ ID NO:3, SEQ ID NO:4, and combinations thereof, and wherein the polynucleotide is present in an expression vector.

2. The composition of claim 1, wherein the polynucleotide encodes each of the amino acid sequences of SEQ ID NO:1, SEQ ID NO:2, SEQ ID NO:3 and SEQ ID NO:4.

3. The composition of claim 1, wherein the polynucleotide encodes the amino acid sequences of SEQ ID NO:9, SEQ ID NO:10 and SEQ ID NO:4.

4. The composition of claim 3, wherein the polynucleotide also encodes the amino acid sequences of SEQ ID NO:11, SEQ ID NO:12, SEQ ID NO:13, SEQ ID NO:14 and SEQ ID NO:15.

5. The composition of claim 1, wherein the polynucleotide is present in a eukaryotic cell in culture.

6. The composition of claim 5, wherein the eukaryotic cell in culture is an epithelial-derived monkey kidney, or a porcine pulmonary alveolar macrophage.

7. A method for stimulating an immune response against Porcine reproductive and respiratory syndrome virus (PRRSV) in a swine comprising administering to the swine a composition comprising a pharmaceutically acceptable carrier or excipient and an isolated Porcine reproductive and respiratory syndrome virus (PRRSV) virion, wherein the virion comprises a polynucleotide encoding amino acid sequences selected from the group of amino acid sequences consisting of SEQ ID NO:1, SEQ ID NO:2, SEQ ID NO:3, SEQ ID NO:4, and combinations thereof.

8. The method of claim 7, wherein the polynucleotide encodes each of the amino acid sequences of SEQ ID NO:1, SEQ ID NO:2, SEQ ID NO:3 and SEQ ID NO:4.

9. The method of claim 8, wherein the polynucleotide encodes SEQ ID NO:9, SEQ ID NO:10, SEQ ID NO:4, SEQ ID NO:11, SEQ ID NO:12, SEQ ID NO:13, SEQ ID NO:14 and SEQ ID NO:15.

* * * * *

SEQUENCE LISTING

```
<160> NUMBER OF SEQ ID NOS: 18

<210> SEQ ID NO 1
<211> LENGTH: 45
<212> TYPE: PRT
<213> ORGANISM: Porcine reproductive and respiratory syndrome virus
      (PRRSV)

<400> SEQUENCE: 1

Ala Ala Lys Leu Ser Val Glu Gln Ala Leu Gly Met Met Asn Val Asp
1               5                   10                  15

Gly Glu Leu Ser Ala Lys Glu Leu Glu Lys Leu Lys Arg Ile Ile Asp
            20                  25                  30

Lys Leu Gln Gly Leu Thr Lys Glu Gln Cys Leu Asn Cys
        35                  40                  45

<210> SEQ ID NO 2
<211> LENGTH: 441
<212> TYPE: PRT
<213> ORGANISM: PRRSV

<400> SEQUENCE: 2

Gly Lys Lys Ala Arg Val Cys Gly Tyr Cys Gly Ala Leu Ala Pro Tyr
1               5                   10                  15

Ala Thr Ala Cys Gly Leu Asp Val Cys Ile Tyr His Thr His Phe His
            20                  25                  30

Gln His Cys Pro Val Thr Ile Trp Cys Gly His Pro Ala Gly Ser Gly
        35                  40                  45
```

```
Ser Cys Ser Glu Cys Lys Ser Pro Val Gly Lys Gly Thr Ser Pro Leu
 50                  55                  60

Asp Glu Val Leu Glu Gln Val Pro Tyr Lys Pro Arg Thr Val Ile
 65                  70                  75                  80

Met His Val Glu Gln Gly Leu Thr Pro Leu Asp Pro Gly Arg Tyr Gln
                     85                  90                  95

Thr Arg Arg Gly Leu Val Ser Val Arg Arg Gly Ile Arg Gly Asn Glu
                100                 105                 110

Val Glu Leu Pro Asp Gly Asp Tyr Ala Ser Thr Ala Leu Leu Pro Thr
                115                 120                 125

Cys Lys Glu Ile Asn Met Val Ala Val Ala Ser Asn Val Leu Arg Ser
130                 135                 140

Arg Phe Ile Ile Gly Pro Pro Gly Ala Gly Lys Thr Tyr Trp Leu Leu
145                 150                 155                 160

Gln Gln Val Gln Asp Gly Asp Val Ile Tyr Thr Pro Thr His Gln Thr
                165                 170                 175

Met Leu Asp Met Ile Arg Ala Leu Gly Thr Cys Arg Phe Asn Val Pro
                180                 185                 190

Ala Gly Thr Thr Leu Gln Phe Pro Val Pro Ser Arg Thr Gly Pro Trp
                195                 200                 205

Val Arg Ile Leu Ala Gly Gly Trp Cys Pro Gly Lys Asn Ser Phe Leu
210                 215                 220

Asp Glu Ala Ala Tyr Cys Asn His Leu Asp Val Leu Arg Leu Leu Ser
225                 230                 235                 240

Lys Thr Thr Leu Thr Cys Leu Gly Asp Phe Lys Gln Leu His Pro Val
                245                 250                 255

Gly Phe Asp Ser His Cys Tyr Val Phe Asp Ile Met Pro Gln Thr Gln
                260                 265                 270

Leu Lys Thr Ile Trp Arg Phe Gly Gln Asn Ile Cys Asp Ala Ile Gln
                275                 280                 285

Pro Asp Tyr Arg Asp Lys Leu Met Ser Met Val Asn Thr Thr Arg Val
                290                 295                 300

Thr Tyr Val Glu Lys Pro Val Arg Tyr Gly Gln Val Leu Thr Pro Tyr
305                 310                 315                 320

His Arg Asp Arg Glu Asp Asp Ala Ile Thr Ile Asp Ser Ser Gln Gly
                325                 330                 335

Ala Thr Phe Asp Val Val Thr Leu His Leu Pro Thr Lys Asp Ser Leu
                340                 345                 350

Asn Arg Gln Arg Ala Leu Val Ala Ile Thr Arg Ala Arg His Ala Ile
                355                 360                 365

Phe Val Tyr Asp Pro His Arg Gln Leu Gln Gly Leu Phe Asp Leu Pro
370                 375                 380

Ala Lys Gly Thr Pro Val Asn Leu Ala Val His Arg Asp Gly Gln Leu
385                 390                 395                 400

Ile Val Leu Asp Arg Asn Asn Lys Glu Cys Thr Val Ala Gln Ala Leu
                405                 410                 415

Gly Asn Gly Asp Lys Phe Arg Ala Thr Asp Lys Arg Val Val Asp Ser
                420                 425                 430

Leu Arg Ala Ile Cys Ala Asp Leu Glu
                435                 440

<210> SEQ ID NO 3
<211> LENGTH: 153
```

<212> TYPE: PRT
<213> ORGANISM: PRRSV

<400> SEQUENCE: 3

```
Gly Arg Tyr Phe Thr Trp Tyr Gln Leu Ala Ser Tyr Ala Ser Tyr Ile
1               5                   10                  15

Arg Val Pro Val Asn Ser Thr Val Tyr Leu Asp Pro Cys Met Gly Pro
            20                  25                  30

Ala Leu Cys Asn Arg Arg Val Val Gly Ser Thr His Trp Gly Ala Asp
        35                  40                  45

Leu Ala Val Thr Pro Tyr Asp Tyr Gly Ala Lys Ile Ile Leu Ser Ser
    50                  55                  60

Ala Tyr His Gly Glu Met Pro Pro Gly Tyr Lys Ile Leu Ala Cys Ala
65                  70                  75                  80

Glu Phe Ser Leu Asp Asp Pro Val Lys Tyr Lys His Thr Trp Gly Phe
                85                  90                  95

Glu Ser Asp Thr Ala Tyr Leu Tyr Glu Phe Thr Gly Asn Gly Glu Asp
            100                 105                 110

Trp Glu Asp Tyr Asn Asp Ala Phe Arg Ala Arg Gln Glu Gly Lys Ile
        115                 120                 125

Tyr Lys Ala Thr Ala Thr Gly Leu Lys Phe Tyr Phe Pro Pro Gly Pro
    130                 135                 140

Val Ile Glu Pro Thr Leu Gly Leu Asn
145                 150
```

<210> SEQ ID NO 4
<211> LENGTH: 254
<212> TYPE: PRT
<213> ORGANISM: PRRSV

<400> SEQUENCE: 4

```
Met Val Asn Ser Cys Thr Phe Leu His Ile Phe Leu Cys Cys Ser Phe
1               5                   10                  15

Leu Tyr Ser Phe Cys Cys Ala Val Val Ala Gly Ser Asn Thr Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Thr
    50                  55                  60

Glu Ile Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Val Val Pro Pro
                85                  90                  95

Gly Leu Ser Ser Glu Gly His Leu Thr Gly Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190
```

```
Val Leu Asn Val Ser Trp Phe Leu Arg Arg Ser Pro Ala Asn His Val
        195                 200                 205

Ser Val Arg Val Leu Gln Ile Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 5
<211> LENGTH: 138
<212> TYPE: DNA
<213> ORGANISM: PRRSV

<400> SEQUENCE: 5
gctgcaaagc tttccgtgga gcaggcccta ggtatgatga atgtcgacgg cgaactgtct      60
gccaaagaac tggagaaact gaaaagaata attgacaaac tccagggcct gactaaggag     120
cagtgtttaa actgctag                                                    138

<210> SEQ ID NO 6
<211> LENGTH: 1323
<212> TYPE: DNA
<213> ORGANISM: PRRSV

<400> SEQUENCE: 6
gggaagaagg cgagagtgtg cgggtactgc ggggccctgg ccccgtacgc tactgcctgt      60
ggcctcgacg tctgcattta ccacacccac ttccaccagc attgtccagt cacaatctgg     120
tgtggccatc cagcgggttc tggttcttgt agtgagtgca atcccctgt agggaaaggc      180 acaagccctt tagacgaggt gctggaacaa gtcccgtata gccccccacg accgttatc      240 atgcatgtgg agcagggtct cacccccctt gatccaggta gataccaaac tcgccgcgga     300
ttagtctctg tcaggcgtgg aattagggga atgaagttg aactaccaga cggtgattat      360
gctagcaccg ccttgctccc tacctgcaaa gagatcaaca tggtcgctgt cgcttccaac     420
gtattgcgca gcaggttcat catcggccca cccggtgctg gaaaacata ctggctcctt      480 caacaggtcc aggatggtga tgttattac acaccaactc accagaccat gcttgacatg     540
attgggcttt gggacgtg ccggttcaac gtcccggcag gcacaacgct gcaattcccc      600
gtcccctccc gcaccggtcc gtgggttcgc atcctagccg gcggttggtg tcctggcaag     660
aattccttcc tagatgaagc agcgtattgc aatcaccttg atgttttgag gcttcttagt      720
aaaactaccc tcacctgtct aggagacttc aagcaactcc acccagtggg ttttgattct     780
cattgctatg tttttgacat catgcctcaa actcaactga agaccatctg gaggtttgga     840
cagaatatct gtgatgccat tcagccagat tacagggaca aactcatgtc catggtcaac     900 acaaccccgtg tgacctacgt ggaaaaacct gtcaggtatg gcaggtcct cacccccctac     960 cacagggacc gagaggacga cgccatcact attgactcca gtcaaggcgc gcacattcgat    1020 gtggttacat tgcatttgcc cactaaagat tcactcaaca ggcaaagagc ccttgttgcc     1080
atcaccaggg caagacacgc tatctttgtg tatgacccac acaggcagct gcagggcttg    1140
tttgatcttc ctgcaaaagg cacacccgtc aacctcgcag tgcaccgcga cgggcagctg    1200
atcgtgctgg atagaaataa caagaatgc acggttgctc aggctctagg caacggggat    1260
aaatttaggg ccacagacaa gcgtgttgta gattctctcc gcgccatttg tgctgatcta    1320
gaa                                                                  1323
```

<210> SEQ ID NO 7
<211> LENGTH: 462
<212> TYPE: DNA
<213> ORGANISM: PRRSV

<400> SEQUENCE: 7

```
ggtcgctatt tcacctggta tcagcttgcc agctatgcct cgtacatccg tgttcctgtc      60
aactctacgg tgtacttgga cccctgcatg ggccccgccc tttgcaacag gagagtcgtc     120
gggtccaccc actgggggc tgacctcgcg gtcaccccct tatgattacgg cgctaaaatt     180
atcctgtcta gcgcgtacca tggtgaaatg ccccccggat acaaaattct ggcgtgcgcg     240
gagttctcgt tggatgaccc agttaagtac aaacatacct ggggggtttga atcggataca     300
gcgtatctgt atgagttcac cggaaacggt gaggactggg aggattacaa tgatgcgttt     360
cgtgcgcgcc aggaagggaa aatttataag gccactgcca ccggcttgaa gttttatttt     420
cccccgggcc ctgtcattga accaacttta ggcctgaatt ga                        462
```

<210> SEQ ID NO 8
<211> LENGTH: 765
<212> TYPE: DNA
<213> ORGANISM: PRRSV

<400> SEQUENCE: 8

```
atggttaata gctgtacatt cctccatatt ttcctctgtt gcagcttctt gtactctttt      60
tgttgtgctg tggttgcggg ttccaatact acgtactgtt tttggtttcc gctggttagg     120
ggcaattttt ctttcgaact cacagtgaat tacacggtgt gtccaccttg cctcacccgg     180
caagcagcca cagagatcta cgaacccggt aggtctcttt ggtgcaggat agggtatgac     240
cgatgtgggg aggacgatca tgacgagcta gggtttgtgg taccgcctgg cctctccagc     300
gaaggccact tgactggtgt ttacgcctgg ttggcgttct tgtccttcag ctacacggcc     360
cagttccatc ccgagatatt cgggataggg aatgtgagtc gagtttatgt tgacatcaaa     420
catcaactca tctgcgccga acatgacggg cagaacacca ccttgcctcg tcatgacaac     480
atttcagccg tgtttcagac ctattaccaa catcaagtcg acggcggcaa ttggtttcac     540
ctagaatggc ttcgtccctt cttttcctcg tggttggttt taaatgtctc ttggtttctc     600
aggcgttcgc ctgcaaacca tgtttcagtt cgagtcttgc agatattaag accaacacca     660
ccgcagcggc aagctttgct gtcctccaag acatcagttg ccttaggcat cgcgactcgg     720
cctctgaggc gattcgcaaa atccctcagt gccgtacggc gatag                     765
```

<210> SEQ ID NO 9
<211> LENGTH: 2503
<212> TYPE: PRT
<213> ORGANISM: PRRSV

<400> SEQUENCE: 9

```
Met Ser Gly Ile Leu Asp Arg Cys Thr Cys Thr Pro Asn Ala Arg Val
  1               5                  10                  15

Phe Met Ala Glu Gly Gln Val Tyr Cys Thr Arg Cys Leu Ser Ala Arg
             20                  25                  30

Ser Leu Leu Pro Leu Asn Leu Gln Val Ser Glu Leu Gly Val Leu Gly
         35                  40                  45

Leu Phe Tyr Arg Pro Glu Glu Pro Leu Arg Trp Thr Leu Pro Arg Ala
     50                  55                  60
```

```
Phe Pro Thr Val Glu Cys Ser Pro Ala Gly Ala Cys Trp Leu Ser Ala
 65                  70                  75                  80

Ile Phe Pro Ile Ala Arg Met Thr Ser Gly Asn Leu Asn Phe Gln Gln
                 85                  90                  95

Arg Met Val Arg Val Ala Ala Glu Leu Tyr Arg Ala Gly Gln Leu Thr
            100                 105                 110

Pro Ala Val Leu Lys Ala Leu Gln Val Tyr Glu Arg Gly Cys Arg Trp
        115                 120                 125

Tyr Pro Ile Val Gly Pro Val Pro Gly Val Ala Val Phe Ala Asn Ser
    130                 135                 140

Leu His Val Ser Asp Lys Pro Phe Pro Gly Ala Thr His Val Leu Thr
145                 150                 155                 160

Asn Leu Pro Leu Pro Gln Arg Pro Lys Pro Glu Asp Phe Cys Pro Phe
                165                 170                 175

Glu Cys Ala Met Ala Thr Val Tyr Asp Ile Gly His Asp Ala Val Met
            180                 185                 190

Tyr Val Ala Glu Arg Lys Val Ser Trp Ala Pro Arg Gly Gly Asp Glu
        195                 200                 205

Val Lys Phe Glu Ala Val Pro Gly Glu Leu Lys Leu Ile Ala Asn Arg
    210                 215                 220

Leu Arg Thr Ser Phe Pro Pro His His Thr Val Asp Met Ser Lys Phe
225                 230                 235                 240

Ala Phe Thr Ala Pro Gly Cys Gly Val Ser Met Arg Val Glu Arg Gln
                245                 250                 255

His Gly Cys Leu Pro Ala Asp Thr Val Pro Glu Gly Asn Cys Trp Trp
            260                 265                 270

Ser Leu Phe Asp Leu Leu Pro Leu Glu Val Gln Asn Lys Glu Ile Arg
        275                 280                 285

His Ala Asn Gln Phe Gly Tyr Gln Thr Lys His Gly Val Ser Gly Lys
    290                 295                 300

Tyr Leu Gln Arg Arg Leu Gln Val Asn Gly Leu Arg Ala Val Thr Asp
305                 310                 315                 320

Leu Asn Gly Pro Ile Val Val Gln Tyr Phe Ser Val Lys Glu Ser Trp
                325                 330                 335

Ile Arg His Leu Lys Leu Ala Gly Glu Pro Ser Tyr Ser Gly Phe Glu
            340                 345                 350

Asp Leu Leu Arg Ile Arg Val Glu Pro Asn Thr Ser Pro Leu Ala Asp
        355                 360                 365

Lys Glu Glu Lys Ile Phe Arg Phe Gly Ser His Lys Trp Tyr Gly Ala
    370                 375                 380

Gly Lys Arg Ala Arg Lys Ala Arg Ser Cys Ala Thr Ala Thr Val Ala
385                 390                 395                 400

Gly Arg Ala Leu Ser Val Arg Glu Thr Arg Gln Ala Lys Glu His Glu
                405                 410                 415

Val Ala Gly Ala Asn Lys Ala Glu His Leu Lys His Tyr Ser Pro Pro
            420                 425                 430

Ala Glu Gly Asn Cys Gly Trp His Cys Ile Ser Ala Ile Ala Asn Arg
        435                 440                 445

Met Val Asn Ser Lys Phe Glu Thr Thr Leu Pro Glu Arg Val Arg Pro
    450                 455                 460

Pro Asp Asp Trp Ala Thr Asp Glu Asp Leu Val Asn Ala Ile Gln Ile
465                 470                 475                 480

Leu Arg Leu Pro Ala Ala Leu Asp Arg Asn Gly Ala Cys Thr Ser Ala
```

-continued

```
                485                 490                 495
Lys Tyr Val Leu Lys Leu Glu Gly Glu His Trp Thr Val Thr Val Thr
                500                 505                 510
Pro Gly Met Ser Pro Ser Leu Leu Pro Leu Glu Cys Val Gln Gly Cys
                515                 520                 525
Cys Gly His Lys Gly Gly Leu Gly Ser Pro Asp Ala Val Glu Val Ser
            530                 535                 540
Gly Phe Asp Pro Ala Cys Leu Asp Arg Leu Ala Glu Val Met His Leu
545                 550                 555                 560
Pro Ser Ser Ala Ile Pro Ala Leu Ala Glu Met Ser Gly Asp Ser
                565                 570                 575
Asp Arg Ser Ala Ser Pro Val Thr Thr Val Trp Thr Val Ser Gln Phe
            580                 585                 590
Phe Ala Arg His Ser Gly Gly Asn His Pro Asp Gln Val Arg Leu Gly
            595                 600                 605
Lys Ile Ile Ser Leu Cys Gln Val Ile Glu Asp Cys Cys Cys Ser Gln
610                 615                 620
Asn Lys Thr Asn Arg Val Thr Pro Glu Glu Val Ala Ala Lys Ile Asp
625                 630                 635                 640
Leu Tyr Leu Arg Gly Ala Thr Asn Leu Glu Glu Cys Leu Ala Arg Leu
                645                 650                 655
Glu Lys Ala Arg Pro Pro Arg Val Ile Asp Thr Ser Phe Asp Trp Asp
            660                 665                 670
Val Val Leu Pro Gly Val Glu Ala Ala Thr Gln Thr Ile Lys Leu Pro
            675                 680                 685
Gln Val Asn Gln Cys Arg Ala Leu Val Pro Val Thr Gln Lys Ser
            690                 695                 700
Leu Asp Asn Asn Ser Val Pro Leu Thr Ala Phe Ser Leu Ala Asn Tyr
705                 710                 715                 720
Tyr Tyr Arg Ala Gln Gly Asp Glu Val Arg His Arg Glu Arg Leu Thr
                725                 730                 735
Ala Val Leu Ser Lys Leu Glu Lys Val Arg Glu Glu Tyr Gly Leu
            740                 745                 750
Met Pro Thr Glu Pro Gly Pro Arg Pro Thr Leu Pro Arg Gly Leu Asp
            755                 760                 765
Glu Leu Lys Asp Gln Met Glu Glu Asp Leu Leu Lys Leu Ala Asn Ala
            770                 775                 780
Gln Thr Thr Ser Asp Met Met Ala Trp Ala Val Glu Gln Val Asp Leu
785                 790                 795                 800
Lys Thr Trp Val Lys Asn Tyr Pro Arg Trp Thr Pro Pro Pro Pro
                805                 810                 815
Pro Lys Val Gln Pro Arg Lys Thr Lys Pro Val Lys Ser Leu Pro Glu
            820                 825                 830
Arg Lys Pro Val Pro Ala Pro Arg Arg Lys Val Gly Ser Asp Cys Gly
            835                 840                 845
Ser Pro Val Ser Leu Gly Gly Asp Val Pro Asn Ser Trp Glu Asp Leu
850                 855                 860
Ala Val Ser Ser Pro Phe Asp Leu Pro Thr Pro Glu Pro Ala Thr
865                 870                 875                 880
Pro Ser Ser Glu Leu Val Ile Val Ser Ser Pro Gln Cys Ile Phe Arg
                885                 890                 895
Pro Ala Thr Pro Leu Ser Glu Pro Ala Pro Ile Pro Ala Pro Arg Gly
            900                 905                 910
```

-continued

```
Thr Val Ser Arg Pro Val Thr Pro Leu Ser Glu Pro Ile Pro Val Pro
            915                 920                 925

Ala Pro Arg Arg Lys Phe Gln Gln Val Lys Arg Leu Ser Ser Ala Ala
930                 935                 940

Ala Ile Pro Pro Tyr Gln Asp Glu Pro Leu Asp Leu Ser Ala Ser Ser
945                 950                 955                 960

Gln Thr Glu Tyr Glu Ala Ser Pro Pro Ala Pro Pro Gln Ser Gly Gly
            965                 970                 975

Val Leu Gly Val Glu Gly His Glu Ala Glu Thr Leu Ser Glu Ile
            980                 985                 990

Ser Asp Met Ser Gly Asn Ile Lys Pro Ala Ser Val Ser Ser Ser Ser
            995                 1000                1005

Ser Leu Ser Ser Val Arg Ile Thr Arg Pro Lys Tyr Ser Ala Gln
    1010                1015                1020

Ala Ile Ile Asp Ser Gly Gly Pro Cys Ser Gly His Leu Gln Glu
    1025                1030                1035

Val Lys Glu Thr Cys Leu Ser Val Met Arg Glu Ala Cys Asp Ala
    1040                1045                1050

Thr Lys Leu Asp Asp Pro Ala Thr Gln Glu Trp Leu Ser Arg Met
    1055                1060                1065

Trp Asp Arg Val Asp Met Leu Thr Trp Arg Asn Thr Ser Val Tyr
    1070                1075                1080

Gln Ala Ile Cys Thr Leu Asp Gly Arg Leu Lys Phe Leu Pro Lys
    1085                1090                1095

Met Ile Leu Glu Thr Pro Pro Tyr Pro Cys Glu Phe Val Met
    1100                1105                1110

Met Pro His Thr Pro Ala Pro Ser Val Gly Ala Glu Ser Asp Leu
    1115                1120                1125

Thr Ile Gly Ser Val Ala Thr Glu Asp Val Pro Arg Ile Leu Glu
    1130                1135                1140

Lys Ile Glu Asn Val Gly Glu Met Ala Asn Gln Gly Pro Leu Ala
    1145                1150                1155

Phe Ser Glu Asp Lys Pro Val Asp Asp Gln Leu Val Asn Asp Pro
    1160                1165                1170

Arg Ile Ser Ser Arg Arg Pro Asp Glu Ser Thr Ser Ala Pro Ser
    1175                1180                1185

Ala Gly Thr Gly Gly Ala Gly Ser Phe Thr Asp Leu Pro Pro Ser
    1190                1195                1200

Asp Gly Ala Asp Ala Asp Gly Gly Pro Phe Arg Thr Val Lys
    1205                1210                1215

Arg Lys Ala Glu Arg Leu Phe Asp Gln Leu Ser Arg Gln Val Phe
    1220                1225                1230

Asp Leu Val Ser His Leu Pro Val Phe Phe Ser Arg Leu Phe Tyr
    1235                1240                1245

Pro Gly Gly Gly Tyr Ser Pro Gly Asp Trp Gly Phe Ala Ala Phe
    1250                1255                1260

Thr Leu Leu Cys Leu Phe Leu Cys Tyr Ser Tyr Pro Ala Phe Gly
    1265                1270                1275

Ile Ala Pro Leu Leu Gly Val Phe Ser Gly Ser Ser Arg Arg Val
    1280                1285                1290

Arg Met Gly Val Phe Gly Cys Trp Leu Ala Phe Ala Val Gly Leu
    1295                1300                1305
```

```
Phe Lys Pro Val Ser Asp Pro Val Gly Ala Ala Cys Glu Phe Asp
    1310            1315              1320
Ser Pro Glu Cys Arg Asn Ile Leu His Ser Phe Glu Leu Leu Lys
    1325            1330              1335
Pro Trp Asp Pro Val Arg Ser Leu Val Val Gly Pro Val Gly Leu
    1340            1345              1350
Gly Leu Ala Ile Leu Gly Arg Leu Leu Gly Gly Ala Arg Cys Ile
    1355            1360              1365
Trp His Phe Leu Leu Arg Leu Gly Ile Val Ala Asp Cys Ile Leu
    1370            1375              1380
Ala Gly Ala Tyr Val Leu Ser Gln Gly Arg Cys Lys Lys Cys Trp
    1385            1390              1395
Gly Ser Cys Ile Arg Thr Ala Pro Asn Glu Val Ala Phe Asn Val
    1400            1405              1410
Phe Pro Phe Thr Arg Ala Thr Arg Ser Ser Leu Ile Asp Leu Cys
    1415            1420              1425
Asp Arg Phe Cys Ala Pro Lys Gly Met Asp Pro Ile Phe Leu Ala
    1430            1435              1440
Thr Gly Trp Arg Gly Cys Trp Ala Gly Arg Ser Pro Ile Glu Gln
    1445            1450              1455
Pro Ser Glu Lys Pro Ile Ala Phe Ala Gln Leu Asp Glu Lys Lys
    1460            1465              1470
Ile Thr Ala Arg Thr Val Val Ala Gln Pro Tyr Asp Pro Asn Gln
    1475            1480              1485
Ala Val Lys Cys Leu Arg Val Leu Gln Ala Gly Gly Ala Met Val
    1490            1495              1500
Ala Lys Ala Val Pro Lys Val Val Lys Val Ser Ala Val Pro Phe
    1505            1510              1515
Arg Ala Pro Phe Phe Pro Thr Gly Val Lys Val Asp Pro Asp Cys
    1520            1525              1530
Arg Val Val Val Asp Pro Asp Thr Phe Thr Ala Ala Leu Arg Ser
    1535            1540              1545
Gly Tyr Ser Thr Thr Asn Leu Val Leu Gly Val Gly Asp Phe Ala
    1550            1555              1560
Gln Leu Asn Gly Leu Lys Ile Arg Gln Ile Ser Lys Pro Ser Gly
    1565            1570              1575
Gly Gly Pro His Leu Met Ala Ala Leu His Val Ala Cys Ser Met
    1580            1585              1590
Ala Leu His Met Leu Ala Gly Ile Tyr Val Thr Ala Val Gly Ser
    1595            1600              1605
Cys Gly Thr Gly Thr Asn Asp Pro Trp Cys Ala Asn Pro Phe Ala
    1610            1615              1620
Val Pro Gly Tyr Gly Pro Gly Ser Leu Cys Thr Ser Arg Leu Cys
    1625            1630              1635
Ile Ser Gln His Gly Leu Thr Leu Pro Leu Thr Ala Leu Val Ala
    1640            1645              1650
Gly Phe Gly Ile Gln Glu Ile Ala Leu Val Val Leu Ile Phe Val
    1655            1660              1665
Ser Ile Gly Gly Met Ala His Arg Leu Ser Cys Lys Ala Asp Met
    1670            1675              1680
Leu Cys Val Leu Leu Ala Ile Ala Ser Tyr Val Trp Val Pro Leu
    1685            1690              1695
Thr Trp Leu Leu Cys Val Phe Pro Cys Trp Leu Arg Cys Phe Ser
```

-continued

```
            1700                1705                1710
Leu His Pro Leu Thr Ile Leu Trp Leu Val Phe Phe Leu Ile Ser
            1715                1720                1725

Val Asn Met Pro Ser Gly Ile Leu Ala Met Val Leu Leu Val Ser
            1730                1735                1740

Leu Trp Leu Leu Gly Arg Tyr Thr Asn Val Ala Gly Leu Val Thr
            1745                1750                1755

Pro Tyr Asp Ile His His Tyr Thr Ser Gly Pro Arg Gly Val Ala
            1760                1765                1770

Ala Leu Ala Thr Ala Pro Asp Gly Thr Tyr Leu Ala Ala Val Arg
            1775                1780                1785

Arg Ala Ala Leu Thr Gly Arg Thr Met Leu Phe Thr Pro Ser Gln
            1790                1795                1800

Leu Gly Ser Leu Leu Glu Gly Ala Phe Arg Thr Arg Lys Pro Ser
            1805                1810                1815

Leu Asn Thr Val Asn Val Ile Gly Ser Ser Met Gly Ser Gly Gly
            1820                1825                1830

Val Phe Thr Ile Asp Gly Lys Val Lys Cys Val Thr Ala Ala His
            1835                1840                1845

Val Leu Thr Gly Asn Ser Ala Arg Val Ser Gly Val Gly Phe Asn
            1850                1855                1860

Gln Met Leu Asp Phe Asp Val Lys Gly Asp Phe Ala Ile Ala Asp
            1865                1870                1875

Cys Pro Asn Trp Gln Gly Ala Ala Pro Lys Thr Gln Phe Cys Thr
            1880                1885                1890

Asp Gly Trp Thr Gly Arg Ala Tyr Trp Leu Thr Ser Ser Gly Val
            1895                1900                1905

Glu Pro Gly Val Ile Gly Lys Gly Phe Ala Phe Cys Phe Thr Ala
            1910                1915                1920

Cys Gly Asp Ser Gly Ser Pro Val Ile Thr Glu Ala Gly Glu Leu
            1925                1930                1935

Val Gly Val His Thr Gly Ser Asn Lys Gln Gly Gly Gly Ile Val
            1940                1945                1950

Thr Arg Pro Ser Gly Gln Phe Cys Asn Val Ala Pro Ile Lys Leu
            1955                1960                1965

Ser Glu Leu Ser Glu Phe Phe Ala Gly Pro Lys Val Pro Leu Gly
            1970                1975                1980

Asp Val Lys Val Gly Ser His Ile Ile Lys Asp Ile Ser Glu Val
            1985                1990                1995

Pro Ser Asp Leu Cys Ala Leu Leu Ala Ala Lys Pro Glu Leu Glu
            2000                2005                2010

Gly Gly Leu Ser Thr Val Gln Leu Leu Cys Val Phe Phe Leu Leu
            2015                2020                2025

Trp Arg Met Met Gly His Ala Trp Thr Pro Leu Val Ala Val Ser
            2030                2035                2040

Phe Phe Ile Leu Asn Glu Val Leu Pro Ala Val Leu Val Arg Ser
            2045                2050                2055

Val Phe Ser Phe Gly Met Phe Val Leu Ser Trp Leu Thr Pro Trp
            2060                2065                2070

Ser Ala Gln Val Leu Met Ile Arg Leu Leu Thr Ala Ala Leu Asn
            2075                2080                2085

Arg Asn Arg Trp Ser Leu Ala Phe Phe Ser Leu Gly Ala Val Thr
            2090                2095                2100
```

```
-continued

Gly Phe Val Ala Asp Leu Ala Ala Thr Gln Gly His Pro Leu Gln
2105                2110                2115

Ala Val Met Asn Leu Ser Thr Tyr Ala Phe Leu Pro Arg Met Met
2120                2125                2130

Val Val Thr Ser Pro Val Pro Val Ile Thr Cys Gly Val Val His
2135                2140                2145

Leu Leu Ala Ile Ile Leu Tyr Leu Phe Lys Tyr Arg Gly Leu His
2150                2155                2160

His Ile Leu Val Gly Asp Gly Val Phe Ser Ala Ala Phe Phe Leu
2165                2170                2175

Arg Tyr Phe Ala Glu Gly Lys Leu Arg Glu Gly Val Ser Gln Ser
2180                2185                2190

Cys Gly Met Asn His Glu Ser Leu Thr Gly Ala Leu Ala Met Arg
2195                2200                2205

Leu Asn Asp Glu Asp Leu Asp Phe Leu Met Lys Trp Thr Asp Phe
2210                2215                2220

Lys Cys Phe Val Ser Ala Ser Asn Met Arg Asn Ala Ala Gly Gln
2225                2230                2235

Phe Ile Glu Ala Ala Tyr Ala Lys Ala Leu Arg Val Glu Leu Ala
2240                2245                2250

Gln Leu Val Gln Val Asp Lys Val Arg Gly Thr Leu Ala Lys Leu
2255                2260                2265

Glu Ala Phe Ala Asp Thr Val Ala Pro Gln Leu Ser Pro Gly Asp
2270                2275                2280

Ile Val Val Ala Leu Gly His Thr Pro Val Gly Ser Ile Phe Asp
2285                2290                2295

Leu Lys Val Gly Ser Thr Lys His Thr Leu Gln Ala Ile Glu Thr
2300                2305                2310

Arg Val Leu Ala Gly Ser Lys Met Thr Val Ala Arg Val Val Asp
2315                2320                2325

Pro Thr Pro Thr Pro Pro Ala Pro Val Pro Ile Pro Leu Pro
2330                2335                2340

Pro Lys Val Leu Glu Asn Gly Pro Asn Ala Trp Gly Asp Glu Asp
2345                2350                2355

Arg Leu Asn Lys Lys Arg Arg Arg Met Glu Ala Leu Gly Ile
2360                2365                2370

Tyr Val Met Gly Gly Lys Lys Tyr Gln Lys Phe Trp Asp Lys Asn
2375                2380                2385

Ser Gly Asp Val Phe Tyr Glu Glu Val His Asn Asn Thr Asp Glu
2390                2395                2400

Trp Glu Cys Leu Arg Val Gly Asp Pro Ala Asp Phe Asp Pro Glu
2405                2410                2415

Lys Gly Thr Leu Cys Gly His Val Thr Ile Glu Asn Lys Ala Tyr
2420                2425                2430

His Val Tyr Thr Ser Pro Ser Gly Lys Lys Phe Leu Val Pro Val
2435                2440                2445

Asn Pro Glu Asn Gly Arg Val Gln Trp Glu Ala Ala Lys Leu Ser
2450                2455                2460

Val Glu Gln Ala Leu Gly Met Met Asn Val Asp Gly Glu Leu Ser
2465                2470                2475

Ala Lys Glu Leu Glu Lys Leu Lys Arg Ile Ile Asp Lys Leu Gln
2480                2485                2490
```

```
Gly Leu Thr Lys Glu Gln Cys Leu Asn Cys
    2495                2500
```

<210> SEQ ID NO 10
<211> LENGTH: 1457
<212> TYPE: PRT
<213> ORGANISM: PRRSV

<400> SEQUENCE: 10

```
Leu Ala Ala Ser Asp Leu Thr Arg Cys Gly Arg Gly Leu Val Val
1               5                   10                  15

Thr Glu Thr Ala Val Lys Ile Val Lys Phe His Asn Arg Thr Phe Thr
                20                  25                  30

Leu Gly Pro Val Asn Leu Lys Val Ala Ser Glu Val Glu Leu Lys Asp
        35                  40                  45

Ala Val Glu His Asn Gln His Pro Val Ala Arg Pro Ile Asp Gly Gly
    50                  55                  60

Val Val Leu Leu Arg Ser Ala Val Pro Ser Leu Ile Asp Val Leu Ile
65                  70                  75                  80

Ser Gly Ala Asp Ala Ser Pro Lys Leu Leu Ala His His Gly Pro Gly
                85                  90                  95

Asn Thr Gly Ile Asp Gly Thr Leu Trp Asp Phe Glu Ser Glu Ala Thr
            100                 105                 110

Lys Glu Glu Val Ala Leu Ser Ala Gln Ile Ile Gln Ala Cys Asp Ile
        115                 120                 125

Arg Arg Gly Asp Ala Pro Glu Ile Gly Leu Pro Tyr Lys Leu Tyr Pro
    130                 135                 140

Val Arg Gly Asn Pro Glu Arg Val Lys Gly Val Leu Gln Asn Thr Arg
145                 150                 155                 160

Phe Gly Asp Ile Pro Tyr Lys Thr Pro Ser Asp Thr Gly Ser Pro Val
                165                 170                 175

His Ala Ala Ala Cys Leu Thr Pro Asn Ala Thr Pro Val Thr Asp Gly
            180                 185                 190

Arg Ser Val Leu Ala Thr Thr Met Pro Pro Gly Phe Glu Leu Tyr Val
        195                 200                 205

Pro Thr Ile Pro Ala Ser Val Leu Asp Tyr Leu Asp Ser Arg Pro Asp
    210                 215                 220

Cys Pro Lys Gln Leu Thr Glu His Gly Cys Glu Asp Ala Ala Leu Lys
225                 230                 235                 240

Asp Leu Ser Lys Tyr Asp Leu Ser Thr Gln Gly Phe Val Leu Pro Gly
                245                 250                 255

Val Leu Arg Leu Val Arg Lys Tyr Leu Phe Ala His Val Gly Lys Cys
            260                 265                 270

Pro Pro Val His Arg Pro Ser Thr Tyr Pro Ala Lys Asn Ser Met Ala
        275                 280                 285

Gly Ile Asn Gly Asn Arg Phe Pro Thr Lys Asp Ile Gln Ser Val Pro
    290                 295                 300

Glu Ile Asp Val Leu Cys Ala Gln Ala Val Arg Glu Asn Trp Gln Thr
305                 310                 315                 320

Val Thr Pro Cys Thr Leu Lys Lys Gln Tyr Cys Gly Lys Lys Lys Thr
                325                 330                 335

Arg Thr Ile Leu Gly Thr Asn Asn Phe Ile Ala Leu Ala His Arg Ala
            340                 345                 350

Val Leu Ser Gly Val Thr Gln Gly Phe Met Lys Lys Ala Phe Asn Ser
        355                 360                 365
```

-continued

```
Pro Ile Ala Leu Gly Lys Asn Lys Phe Lys Glu Leu Gln Thr Pro Val
    370                 375                 380

Leu Gly Arg Cys Leu Glu Ala Asp Leu Ala Ser Cys Asp Arg Ser Thr
385                 390                 395                 400

Pro Ala Ile Val Arg Trp Phe Ala Ala Asn Leu Leu Tyr Glu Leu Ala
                405                 410                 415

Cys Ala Glu Glu His Leu Pro Ser Tyr Val Leu Asn Cys Cys His Asp
            420                 425                 430

Leu Leu Val Thr Gln Ser Gly Ala Val Thr Lys Arg Gly Gly Leu Ser
        435                 440                 445

Ser Gly Asp Pro Ile Thr Ser Val Ser Asn Thr Ile Tyr Ser Leu Val
    450                 455                 460

Ile Tyr Ala Gln His Met Val Leu Ser Tyr Phe Lys Ser Gly His Pro
465                 470                 475                 480

His Gly Leu Leu Phe Leu Gln Asp Gln Leu Lys Phe Glu Asp Met Leu
                485                 490                 495

Lys Val Gln Pro Leu Ile Val Tyr Ser Asp Asp Leu Val Leu Tyr Ala
            500                 505                 510

Glu Ser Pro Thr Met Pro Asn Tyr His Trp Trp Val Glu His Leu Asn
        515                 520                 525

Leu Met Leu Gly Phe Gln Thr Asp Pro Lys Lys Thr Ala Ile Thr Asp
    530                 535                 540

Ser Pro Ser Phe Leu Gly Cys Arg Ile Ile Asn Gly Arg Gln Leu Val
545                 550                 555                 560

Pro Asn Arg Asp Arg Ile Leu Ala Ala Leu Ala Tyr His Met Lys Ala
                565                 570                 575

Ser Asn Val Ser Glu Tyr Tyr Ala Ser Ala Ala Ile Leu Met Asp
            580                 585                 590

Ser Cys Ala Cys Leu Glu Tyr Asp Pro Glu Trp Phe Glu Glu Leu Val
        595                 600                 605

Val Gly Ile Ala Gln Cys Ala Arg Lys Asp Gly Tyr Ser Phe Pro Gly
    610                 615                 620

Thr Pro Phe Phe Met Ser Met Trp Glu Lys Leu Arg Ser Asn Tyr Glu
625                 630                 635                 640

Gly Lys Lys Ala Arg Val Cys Gly Tyr Cys Gly Ala Leu Ala Pro Tyr
                645                 650                 655

Ala Thr Ala Cys Gly Leu Asp Val Cys Ile Tyr His Thr His Phe His
            660                 665                 670

Gln His Cys Pro Val Thr Ile Trp Cys Gly His Pro Ala Gly Ser Gly
        675                 680                 685

Ser Cys Ser Glu Cys Lys Ser Pro Val Gly Lys Gly Thr Ser Pro Leu
    690                 695                 700

Asp Glu Val Leu Glu Gln Val Pro Tyr Lys Pro Pro Arg Thr Val Ile
705                 710                 715                 720

Met His Val Glu Gln Gly Leu Thr Pro Leu Asp Pro Gly Arg Tyr Gln
                725                 730                 735

Thr Arg Arg Gly Leu Val Ser Val Arg Arg Gly Ile Arg Gly Asn Glu
            740                 745                 750

Val Glu Leu Pro Asp Gly Asp Tyr Ala Ser Thr Ala Leu Leu Pro Thr
        755                 760                 765

Cys Lys Glu Ile Asn Met Val Ala Val Ala Ser Asn Val Leu Arg Ser
    770                 775                 780
```

```
Arg Phe Ile Ile Gly Pro Pro Gly Ala Gly Lys Thr Tyr Trp Leu Leu
785                 790                 795                 800

Gln Gln Val Gln Asp Gly Asp Val Ile Tyr Thr Pro Thr His Gln Thr
            805                 810                 815

Met Leu Asp Met Ile Arg Ala Leu Gly Thr Cys Arg Phe Asn Val Pro
        820                 825                 830

Ala Gly Thr Thr Leu Gln Phe Pro Val Pro Ser Arg Thr Gly Pro Trp
        835                 840                 845

Val Arg Ile Leu Ala Gly Gly Trp Cys Pro Gly Lys Asn Ser Phe Leu
850                 855                 860

Asp Glu Ala Ala Tyr Cys Asn His Leu Asp Val Leu Arg Leu Leu Ser
865                 870                 875                 880

Lys Thr Thr Leu Thr Cys Leu Gly Asp Phe Lys Gln Leu His Pro Val
                885                 890                 895

Gly Phe Asp Ser His Cys Tyr Val Phe Asp Ile Met Pro Gln Thr Gln
                900                 905                 910

Leu Lys Thr Ile Trp Arg Phe Gly Gln Asn Ile Cys Asp Ala Ile Gln
        915                 920                 925

Pro Asp Tyr Arg Asp Lys Leu Met Ser Met Val Asn Thr Thr Arg Val
930                 935                 940

Thr Tyr Val Glu Lys Pro Val Arg Tyr Gly Gln Val Leu Thr Pro Tyr
945                 950                 955                 960

His Arg Asp Arg Glu Asp Asp Ala Ile Thr Ile Asp Ser Ser Gln Gly
                965                 970                 975

Ala Thr Phe Asp Val Val Thr Leu His Leu Pro Thr Lys Asp Ser Leu
        980                 985                 990

Asn Arg Gln Arg Ala Leu Val Ala Ile Thr Arg Ala Arg His Ala Ile
        995                 1000                1005

Phe Val Tyr Asp Pro His Arg Gln Leu Gln Gly Leu Phe Asp Leu
    1010                1015                1020

Pro Ala Lys Gly Thr Pro Val Asn Leu Ala Val His Arg Asp Gly
    1025                1030                1035

Gln Leu Ile Val Leu Asp Arg Asn Asn Lys Glu Cys Thr Val Ala
    1040                1045                1050

Gln Ala Leu Gly Asn Gly Asp Lys Phe Arg Ala Thr Asp Lys Arg
    1055                1060                1065

Val Val Asp Ser Leu Arg Ala Ile Cys Ala Asp Leu Glu Gly Ser
    1070                1075                1080

Ser Ser Pro Leu Pro Lys Val Ala His Asn Leu Gly Phe Tyr Phe
    1085                1090                1095

Ser Pro Asp Leu Thr Gln Phe Ala Lys Leu Pro Val Glu Leu Ala
    1100                1105                1110

Pro His Trp Pro Val Val Thr Thr Gln Asn Asn Glu Lys Trp Pro
    1115                1120                1125

Asp Arg Leu Val Ala Ser Leu Arg Pro Ile His Lys Tyr Ser Arg
    1130                1135                1140

Ala Cys Ile Gly Ala Gly Tyr Met Val Gly Pro Ser Val Phe Leu
    1145                1150                1155

Gly Thr Pro Gly Val Val Ser Tyr Tyr Leu Thr Lys Phe Val Lys
    1160                1165                1170

Gly Glu Ala Gln Val Leu Pro Glu Thr Val Phe Ser Thr Gly Arg
    1175                1180                1185

Ile Glu Val Asp Cys Arg Glu Tyr Leu Asp Asp Arg Glu Arg Glu
```

```
                1190            1195            1200
Val Ala Ala Ser Leu Pro His Ala Phe Ile Gly Asp Val Lys Gly
    1205            1210            1215

Thr Thr Val Gly Gly Cys His His Val Thr Ser Arg Tyr Leu Pro
    1220            1225            1230

Arg Val Leu Pro Lys Glu Ser Val Ala Val Gly Val Ser Ser
    1235            1240            1245

Pro Gly Lys Ala Ala Lys Ala Leu Cys Thr Leu Thr Asp Val Tyr
    1250            1255            1260

Leu Pro Asp Leu Glu Ala Tyr Leu His Pro Glu Thr Gln Ser Lys
    1265            1270            1275

Cys Trp Lys Met Met Leu Asp Phe Lys Glu Val Arg Leu Met Val
    1280            1285            1290

Trp Lys Asp Lys Thr Ala Tyr Phe Gln Leu Glu Gly Arg Tyr Phe
    1295            1300            1305

Thr Trp Tyr Gln Leu Ala Ser Tyr Ala Ser Tyr Ile Arg Val Pro
    1310            1315            1320

Val Asn Ser Thr Val Tyr Leu Asp Pro Cys Met Gly Pro Ala Leu
    1325            1330            1335

Cys Asn Arg Arg Val Val Gly Ser Thr His Trp Gly Ala Asp Leu
    1340            1345            1350

Ala Val Thr Pro Tyr Asp Tyr Gly Ala Lys Ile Ile Leu Ser Ser
    1355            1360            1365

Ala Tyr His Gly Glu Met Pro Pro Gly Tyr Lys Ile Leu Ala Cys
    1370            1375            1380

Ala Glu Phe Ser Leu Asp Asp Pro Val Lys Tyr Lys His Thr Trp
    1385            1390            1395

Gly Phe Glu Ser Asp Thr Ala Tyr Leu Tyr Glu Phe Thr Gly Asn
    1400            1405            1410

Gly Glu Asp Trp Glu Asp Tyr Asn Asp Ala Phe Arg Ala Arg Gln
    1415            1420            1425

Glu Gly Lys Ile Tyr Lys Ala Thr Ala Thr Gly Leu Lys Phe Tyr
    1430            1435            1440

Phe Pro Pro Gly Pro Val Ile Glu Pro Thr Leu Gly Leu Asn
    1445            1450            1455

<210> SEQ ID NO 11
<211> LENGTH: 256
<212> TYPE: PRT
<213> ORGANISM: PRRSV

<400> SEQUENCE: 11

Met Lys Trp Gly Pro Cys Lys Ala Phe Leu Thr Lys Leu Ala Asn Phe
1               5                   10                  15

Leu Trp Met Leu Ser Arg Ser Ser Trp Cys Pro Leu Leu Ile Ser Leu
            20                  25                  30

Tyr Phe Trp Pro Phe Cys Leu Ala Ser Pro Ser Pro Val Gly Trp Trp
        35                  40                  45

Ser Phe Ala Ser Asp Trp Phe Ala Pro Arg Tyr Ser Val Arg Ala Leu
    50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Thr Lys His Pro Leu Gly
                85                  90                  95
```

```
Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Ile Leu Arg Thr
225                 230                 235                 240

Val Phe Gly Phe Arg Trp Leu Gly Ala Ile Phe Leu Ser Asn Ser Gln
                245                 250                 255

<210> SEQ ID NO 12
<211> LENGTH: 178
<212> TYPE: PRT
<213> ORGANISM: PRRSV

<400> SEQUENCE: 12

Met Ala Ser Ser Leu Leu Phe Leu Val Val Gly Phe Lys Cys Leu Leu
1               5                   10                  15

Val Ser Gln Ala Phe Ala Cys Lys Pro Cys Phe Ser Ser Ser Leu Ala
            20                  25                  30

Asp Ile Lys Thr Asn Thr Thr Ala Ala Ala Ser Phe Ala Val Leu Gln
        35                  40                  45

Asp Ile Ser Cys Leu Arg His Arg Asp Ser Ala Ser Glu Ala Ile Arg
    50                  55                  60

Lys Ile Pro Gln Cys Arg Thr Ala Ile Gly Thr Pro Val Tyr Val Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile

<210> SEQ ID NO 13
<211> LENGTH: 200
<212> TYPE: PRT
<213> ORGANISM: PRRSV
```

```
<400> SEQUENCE: 13

Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
                20                  25                  30

Asn Asp Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
                100                 105                 110

Ala Val Cys Ala Leu Ala Ala Leu Thr Cys Phe Val Ile Arg Phe Ala
                115                 120                 125

Lys Asn Cys Met Ser Trp Arg Tyr Ala Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Trp Gly Arg Pro
                195                 200

<210> SEQ ID NO 14
<211> LENGTH: 174
<212> TYPE: PRT
<213> ORGANISM: PRRSV

<400> SEQUENCE: 14

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
                20                  25                  30

Ala Leu Lys Val Ser Arg Gly Arg Leu Leu Gly Leu Leu His Leu Leu
                35                  40                  45

Ile Phe Leu Asn Cys Ala Phe Thr Phe Gly Tyr Met Thr Phe Ala His
50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
                100                 105                 110

Ala His His Val Glu Ser Ala Ala Gly Phe His Pro Ile Ala Ala Asn
                115                 120                 125

Asp Asn His Ala Phe Val Val Arg Arg Pro Gly Ser Thr Thr Val Asn
130                 135                 140

Gly Thr Leu Val Pro Gly Leu Lys Ser Leu Val Leu Gly Gly Arg Lys
145                 150                 155                 160
```

Ala Val Lys Gln Gly Val Val Asn Leu Val Lys Tyr Ala Lys
              165                  170

<210> SEQ ID NO 15
<211> LENGTH: 123
<212> TYPE: PRT
<213> ORGANISM: PRRSV

<400> SEQUENCE: 15

Met Pro Asn Asn Gly Lys Gln Gln Lys Lys Lys Gly Asp Gly
1            5               10              15

Gln Pro Val Asn Gln Leu Cys Gln Met Leu Gly Lys Ile Ile Ala Gln
        20               25              30

Gln Asn Gln Ser Arg Gly Lys Gly Pro Gly Lys Lys Asn Lys Lys Lys
          35              40              45

Asn Pro Glu Lys Pro His Phe Pro Leu Ala Thr Glu Asp Asp Val Arg
    50                 55              60

His His Phe Thr Pro Ser Glu Arg Gln Leu Cys Leu Ser Ser Ile Gln
65              70               75              80

Thr Ala Phe Asn Gln Gly Ala Gly Thr Cys Thr Leu Ser Asp Ser Gly
        85               90              95

Arg Ile Ser Tyr Thr Val Glu Phe Ser Leu Pro Thr His His Thr Val
       100             105            110

Arg Leu Ile Arg Val Thr Ala Ser Pro Ser Ala
       115             120

<210> SEQ ID NO 16
<211> LENGTH: 15470
<212> TYPE: DNA
<213> ORGANISM: PRRSV

<400> SEQUENCE: 16

| | |
|---|---|
| atgacgtata ggtgttggct ctatgccttg gcatttgtat tgtcaggagc tgtgaccatt | 60 |
| ggcacagccc aaaacttgct gcacagaaac acccttctgt gatagcctcc ttcagggag | 120 |
| cttagggttt gtccctagca ccttgcttcc ggagttgcac tgctttacgg tctctccacc | 180 |
| cctttaacca tgtctgggat acttgatcgg tgcacgtgta cccccaatgc cagggtgttt | 240 |
| atggcggagg ccaagtcta ctgcacacga tgcctcagtg cacggtctct ccttcccctg | 300 |
| aacctccaag tttctgagct cggggtgcta ggcctattct acaggcccga gagccactc | 360 |
| cggtggacgt tgccacgtgc attccccact gttgagtgct ccccgccgg ggcctgctgg | 420 |
| ctttctgcaa tctttccaat cgcacgaatg accagtggaa acctgaactt ccaacaaaga | 480 |
| atggtacggg tcgcagctga gctttacaga gccggccagc tcacccctgc agtcttgaag | 540 |
| gctctacaag tttatgaacg gggttgccgc tggtacccca ttgttggacc tgtccctgga | 600 |
| gtggccgttt cgccaattc cctacatgtg agtgataaac ctttcccggg agcaactcac | 660 |
| gtgttgacca acctgccgct cccgcagaga cccaagcctg aagactttg ccccttgag | 720 |
| tgtgctatgg ctactgtcta tgacattggt catgacgccg tcatgtatgt ggccgaaagg | 780 |
| aaagtctcct gggcccctcg tggcggggat gaagtgaaat tgaagctgt ccccggggag | 840 |
| ttgaagttga ttgcgaaccg gctccgcacc tccttcccgc ccaccacac agtggacatg | 900 |
| tctaagttcg ccttcacagc ccctgggtgt ggtgtttcta tgcgggtcga acgccaacac | 960 |
| ggctgccttc ccgctgacac tgtccctgaa gcaactgct ggtggagctt gtttgacttg | 1020 |
| cttccactgg aagttcagaa caagaaatt cgccatgcta accaatttgg ctaccagacc | 1080 |

```
aagcatggtg tctctggcaa gtacctacag cggaggctgc aagttaatgg tctccgagca    1140
gtaactgacc taaacggacc tatcgtcgta cagtacttct ccgttaagga gagttggatc    1200
cgccatttga aactggcggg agaacccagc tactctgggt ttgaggacct cctcagaata    1260
agggttgagc ctaacacgtc gccattggct gacaaggaag aaaaaatttt ccggtttggc    1320
agtcacaagt ggtacggcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt    1500
ggttggcact gcattccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg tgcttgtac tagcgccaag    1680 tacgtactta agctggaagg tgagcattgg actgtcactg tgaccccdtgg gatgtcccct    1740 tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160 aaaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttggacaac aactcggtcc ccctgaccgc cttttcactg    2340
gctaactact actaccgtgc gcaaggtgac gaagttcgtc accgtgaaag actaaccgcc    2400
gtgctctcca gttggaaaa ggttgttcga gaagaatatg gctcatgcc aaccgagcct    2460 ggtccacggc ccacactgcc acgcgggctc gacgaactca agaccagat ggaggaggac    2520 ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agcccctttg atctcccgac ccacctgag    2820 ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct ccccagcac cgccgcagag cggggcgtt    3120 ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcgggcgggc cctgcagtgg gcatctccaa    3300
gaggtaaagg aaacatgcct tagtgtcatg cgcgaggcat gtgatgcgac taagcttgat    3360 gacccctgcta cgcaggaatg gctttctcgc atgtgggatc gggtggacat gctgacttgg    3420
cgcaacacgt ctgtttacca ggcgatttgc acccttagatg gcaggttaaa gttcctccca    3480
```

```
aaaatgatac tcgagacacc gccgccctat ccgtgtgagt ttgtgatgat gcctcacacg   3540
cctgcacctt ccgtaggtgc ggagagcgac cttaccattg gctcagttgc tactgaagat   3600
gttccacgca tcctcgagaa aatagaaaat gtcggcgaga tggccaacca gggacccttg   3660
gccttctccg aggataaacc ggtagatgac caacttgtca acgaccccg gatatcgtcg    3720 cggaggcctg acgagagcac atcagctccg tccgcaggca caggtggcgc cggctctttt   3780
accgatttgc cgccttcaga tggcgcggat gcggacgggg gggggccgtt tcggacggta   3840
aaaagaaaag ctgaaaggct ctttgaccaa ctgagccgtc aggttttga cctcgtctcc     3900 catctccctg ttttcttctc acgccttttc taccctggcg gtggttattc tccgggtgat   3960
tggggttttg cagcttttac tctattgtgc ctcttttat gttacagtta cccagccttt    4020
ggtattgctc ccctcttggg tgtgttttct gggtcttctc ggcgcgttcg aatgggggtt   4080
tttggctgct ggttggcttt tgctgttggt ctgttcaagc ctgtgtccga cccagtcggc   4140
gctgcttgtg agtttgactc gccagagtgt agaaacatcc ttcattcttt tgagcttctc   4200
aaaccttggg accctgttcg cagccttgtt gtgggccccg tcggtctcgg tcttgccatt   4260
cttggcaggt tactgggcgg ggcacgctgc atctggcact ttttgcttag gcttggcatt   4320
gttgcagact gtatcttggc tggagcttac gtgctttctc aaggtaggtg taaaaagtgc   4380
tggggatctt gtataagaac tgctcctaat gaggtcgctt ttaacgtgtt tcctttcaca   4440
cgtgcgacca ggtcgtcact tatcgacctg tgcgatcggt tttgtgcgcc aaaaggaatg   4500
gaccccattt ttctcgccac tgggtggcgc gggtgctggg ccggccgaag ccccattgag   4560
caaccctctg aaaacccat cgcgtttgcc caattggatg aaaagaagat tacggctagg     4620
actgtggtcg cccagcctta tgaccccaac caagccgtaa agtgcttgcg ggtattgcag   4680
gcgggtgggg cgatggtggc taaggcggtc ccaaaagtgg tcaaggtttc cgctgttcca   4740
ttccgagccc ccttctttcc cactggagtg aaagttgacc ctgattgcag ggtcgtggtt   4800
gaccctgaca ctttcactgc agctctccgg tctggctact ccaccacaaa cctcgtcctt   4860
ggtgtagggg actttgccca gctgaatgga ttaaaaatca ggcaaatttc caagccttca   4920
gggggaggcc cacatctcat ggccgccctg catgttgcct gctcgatggc tctgcacatg   4980
cttgctggga tttatgtgac tgcggtgggt tcttgcggca ccggcaccaa cgacccgtgg   5040
tgcgctaacc cgtttgccgt ccctggctac ggacctggct ctctctgcac gtccaggttg   5100
tgcatttccc aacacggcct taccctgccc ttgacagcac ttgtggcggg attcggtatt   5160
caagaaattg ccttggtcgt tttgatttt gtttccatcg gaggcatggc tcataggttg      5220
agctgtaagg ctgacatgct gtgtgttttg cttgcaattg ccagctatgt ttgggtacct   5280
cttacctggt tgctttgtgt gtttccttgc tggttgcgct gttttctttt gcacccctc      5340 accatcctat ggttggtgtt tttcttgatt tctgtgaata tgccttcagg aatcttggcc   5400
atggtgttgt tggtttctct ttggcttctt ggtcgttata ctaatgtcgc tggccttgtc   5460
accccctacg acattcatca ttacaccagt ggccccgcg gtgttgccgc cttggctacc     5520
gcaccagatg ggacctactt ggccgctgtc cgccgcgctg cgttgactgg ccgcaccatg   5580
ctgtttaccc cgtcccagct tgggtctctt cttgagggtc ttttcagaac tcgaaagccc   5640
tcactgaaca ccgtcaatgt gatcgggtcc tccatgggct ctggcggggt gtttaccatc   5700
gacgggaaag tcaagtgcgt aactgccgca catgtcctta cggcaattc agctcgggtt      5760 tccggggtcg gcttcaatca aatgcttgac tttgacgtaa agggagattt cgctatagct   5820
```

```
gattgcccga attggcaagg ggctgccccc aagacccaat tctgcacgga tggatggact      5880
ggccgtgcct attggctaac atcctctggc gtcgaacccg gcgtcattgg aaaaggattc      5940
gccttctgct tcaccgcatg tggcgattcc gggtccccag tgatcaccga ggccggtgag      6000
cttgtcggcg ttcacacggg atcgaataaa caagggggg gcattgttac gcgcccctca       6060
ggccagtttt gtaatgtggc acccatcaag ctaagcgaat taagtgaatt ctttgctggg      6120
cctaaggtcc cgctcggtga tgtgaaggtc ggcagccaca taattaaaga cataagcgag      6180
gtgccttcag atctttgtgc cttgcttgct gccaaacctg aactggaagg aggcctctcc      6240
accgtccaac ttctttgtgt gttttttctc ctgtggagaa tgatgggaca tgcctggacg      6300
cccttggttg ctgtgagttt ctttattttg aatgaggttc tcccagccgt cctggtccgg      6360
agtgttttct cctttggaat gtttgtgcta tcctggctca cgccatggtc tgcgcaagtt      6420
ctgatgatca ggcttctgac agcagctctt aacaggaaca gatggtcact tgcctttttc      6480
agcctcggtg cagtgaccgg ttttgtcgca gatcttgcgg ccactcaggg gcatccgttg      6540
caggcagtga tgaatttgag cacctatgca ttcctgcctc ggatgatggt tgtgacctca      6600
ccagtcccag tgatcacgtg tggtgtcgtg cacctacttg ccatcatttt gtacttgttt      6660
aagtaccgtg gcctgcacca tatccttgtt ggcgatgagg tgttctctgc ggcttttcttc     6720 ttgagatact tgccgaggg aaagttgagg aaggggtgt cgcaatcctg cggaatgaat       6780
catgagtctc tgactggtgc cctcgctatg agactcaatg acgaggactt ggatttcctt      6840
atgaaatgga ctgattttaa gtgctttgtt tctgcgtcca acatgaggaa tgcagcgggt      6900
caatttatcg aggctgccta tgctaaagca cttagagtag aactggccca gttggtgcag      6960
gttgataaag ttcgaggtac tttggccaaa cttgaagctt tgctgatac cgtggcacct       7020 caactctcgc ccggtgacat tgttgtcgct ctcggccaca cgcctgttgg cagtatcttc      7080
gacctaaagg ttggtagcac caagcatacc ctccaagcca ttgagaccag agtccttgct      7140
gggtccaaaa tgaccgtggc gcgcgtcgtc gacccgaccc ccacgccccc acccgcaccc      7200
gtgcccatcc ccctcccacc gaaagttctg gagaatggcc ccaacgcttg gggggatgag      7260
gaccgtttga ataagaagaa gaggcgcagg atggaagccc tcggcatcta tgttatgggc      7320
gggaaaaagt accagaaatt ttgggacaag aattccggtg atgtgttta tgaggaggtc       7380 cataataaca cagatgagtg ggagtgtctc agagttggcg accctgccga cttgacccct      7440
gagaagggga ctctgtgtgg acatgtcacc attgaaaaca aggcttacca tgtttacacc      7500
tccccatctg gtaagaagtt cttggtcccc gtcaacccag agaatggaag agtccaatgg      7560
gaagctgcaa agctttccgt ggagcaggcc ctaggtatga tgaatgtcga cggcgaactg      7620
tctgccaaag aactggagaa actgaaaaga ataattgaca aactccaggg cctgactaag      7680
gagcagtgtt taaactgcta gccgccagcg acttgacccg ctgtggtcgc ggcggcttgg      7740
ttgttactga aacggcggta aaaatagtca aatttcacaa ccggaccttc accctgggac      7800
ctgtgaattt aaaagtggcc agtgaggttg agctaaaaga cgcggttgag cacaaccaac      7860
acccggttgc gagaccgatc gatggtggag ttgtgctcct gcgttccgcg gttccttcgc      7920
ttatagacgt cttgatctcc ggtgctgatg catctcccaa gttacttgcc catcacgggc      7980
cgggaaacac tgggatcgat ggcacgctct gggattttga gtccgaagcc actaaagagg      8040
aagtcgcact cagtgcgcaa ataatacagg cttgtgacat taggcgcggc gacgctcctg      8100
aaattggtct cccttacaag ctgtaccctg ttagggtaa ccctgagcgg gtgaaggag        8160 ttctgcagaa tacaaggttt ggagacatac cttacaaaac ccccagtgac actggaagcc      8220
```

```
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc acccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca    9180
tgctcaaggt tcaacccctg atcgtctatt cggacgacct cgtgctgtat gccgagtctc    9240
ccaccatgcc aaactatcac tggtgggttg aacatctgaa tttgatgctg gggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480 cttgttttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgaaggg aagaaggcga gagtgtgcgg gtactgcggg gccctggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttag acgaggtgct ggaacaagtc ccgtataagc    9840
ccccacggac cgttatcatg catgtggagc agggtctcac cccccttgat ccaggtagat    9900
accaaactcg ccgcggatta gtctctgtca ggcgtggaat taggggaaat gaagttgaac    9960
taccagacgg tgattatgct agcaccgcct tgctccctac ctgcaaagag atcaacatgg   10020
tcgctgtcgc ttccaacgta ttgcgcagca ggttcatcat cggcccaccc ggtgctggga   10080
aaacatactg gctccttcaa caggtccagg atggtgatgt tatttacaca ccaactcacc   10140
agaccatgct tgacatgatt agggctttgg ggacgtgccg gttcaacgtc ccggcaggca   10200
caacgctgca attccccgtc cctcccgca ccggtccgtg ggttcgcatc ctagccggcg   10260
gttggtgtcc tggcaagaat tccttcctag atgaagcagc gtattgcaat caccttgatg   10320
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gttggacag aatatctgtg atgccattca gccagattac agggacaaac   10500
tcatgtccat ggtcaacaca acccgtgtga cctacgtgga aaaacctgtc aggtatgggc   10560
```

```
aggtcctcac cccctaccac agggaccgag aggacgacgc catcactatt gactccagtc   10620
aaggcgccac attcgatgtg gttacattgc atttgcccac taaagattca ctcaacaggc   10680
aaagagccct tgttgccatc accagggcaa gacacgctat ctttgtgtat gacccacaca   10740
ggcagctgca gggcttgttt gatcttcctg caaaaggcac acccgtcaac ctcgcagtgc   10800
accgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actgcccgt ggtgacaacc cagaacaatg aaaagtggcc agatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
aggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg ggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcctgtca actctacggt gtacttggac ccctgcatgg   11700
gccccgccct ttgcaacagg agagtcgtcg ggtccaccca ctgggggggct gacctcgcgg   11760
tcaccccctta tgattacggc gctaaaatta tcctgtctag cgcgtaccat ggtgaaatgc   11820
cccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cggcttgaag ttttattttc cccccgggccc tgtcattgaa ccaactttag   12060
gcctgaattg aaatgaaatg gggtccatgc aaagccttt tgacaaaatt ggccaacttt   12120
ttgtggatgc tttcacggag ttcttggtgt ccattgttga tatcattata ttttttggcca   12180
ttttgtttgg cttcaccatc gccggttggc tggtggtctt ttgcatcaga ttggttttgct   12240
ccgcgatact ccgtacgcgc cctgccattc actctgagca attacagaag atcttatgag   12300
gcctttcttt cccagtgcca agtggacatt cccacctggg gaactaaaca tcctttgggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttga tgtggtggct cattttcagc atctagccgc cattgaagcc   12540
gagacctgta aatatttggc ctcccggctg cccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact ctttttgttg tgctgtggtt gcgggttcca   12780
atactacgta ctgtttttgg tttcgctgg ttaggggcaa ttttttcttc gaactcacag   12840
tgaattacac ggtgtgtcca ccttgcctca cccggcaagc agccacagag atctacgaac   12900
ccggtaggtc tctttggtgc aggataggt atgaccgatg tggggaggac gatcatgacg   12960
```

```
agctagggtt tgtggtaccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acgggcagaa caccaccttg cctcgtcatg acaacatttc agccgtgttt cagacctatt   13200
accaacatca agtcgacggc ggcaattggt ttcacctaga atggcttcgt cccttctttt   13260
cctcgtggtt ggttttaaat gtctcttggt ttctcaggcg ttcgcctgca aaccatgttt   13320
cagttcgagt cttgcagata ttaagaccaa caccaccgca gcggcaagct tgctgtcct   13380 ccaagacatc agttgcctta ggcatcgcga ctcggcctct gaggcgattc gcaaaatccc   13440
tcagtgccgt acggcgatag ggacacccgt gtatgttacc atcacagcca atgtgacaga   13500
tgagaattat ttacattctt ctgatctcct catgctttct tcttgccttt tctatgcttc   13560
tgagatgagt gaaaagggat ttaaggtggt atttggcaat gtgtcaggca tcgtggctgt   13620
gtgtgtcaat tttaccagct acgtccaaca tgttaaggag tttacccaac gctccctggt   13680
ggtcgaccat gtgcggttgc tccatttcat gacacctgag accatgaggt gggcaactgt   13740
tttagcctgt cttttttgcca ttctgttggc aatttgaatg tttaagtatg ttggagaaat   13800
gcttgaccgc gggctgttgc tcgcgattgc tttctttgtg gtgtatcgtg ccgttctgtt   13860
ttgctgtgct cgccaacgcc agcaacgaca gcagctccca tctacagctg atttacaact   13920
tgacgctatg tgagctgaat ggcacagatt ggctagctaa caaatttgat tgggcagtgg   13980
agagttttgt catcttttccc gttttgactc acattgtctc ctatggtgcc ctcactacca   14040
gccatttcct tgacacagtc gctttagtca ctgtgtctac cgccgggttt gttcacgggc   14100
ggtatgtcct aagtagcatc tacgcggtct gtgccctggc tgcgttgact tgcttcgtca   14160
ttaggtttgc aaagaattgc atgtcctggc gctacgcgtg taccagatat accaactttc   14220
ttctggacac taagggcaga ctctatcgtt ggcggtcgcc tgtcatcata gagaaaaggg   14280
gcaaagttga ggtcgaaggt catctgatcg acctcaaaag agttgtgctt gatggttccg   14340
tggcaacccc tataaccaga gtttcagcgg aacaatgggg tcgtccttag atgacttctg   14400
tcatgatagc acggctccac aaaaggtgct tttggcgttt tctattacct acacgccagt   14460
gatgatatat gccctaaagg tgagtcgcgg ccgactgcta gggcttctgc acctttttgat  14520 cttcctgaat tgtgctttca ccttcgggta catgactttc gcgcactttc agagtacaaa   14580
taaggtcgcg ctcactatgg gagcagtagt tgcactcctt tggggggtgt actcagccat   14640
agaaacctgg aaattcatca cctccagatg ccgtttgtgc ttgctaggcc gcaagtacat   14700
tctggcccct gcccaccacg ttgaaagtgc cgcaggcttt catccgattg cggcaaatga   14760
taaccacgca tttgtcgtcc ggcgtcccgg ctccactacg gtcaacggca cattggtgcc   14820
cgggttaaaa agcctcgtgt tgggtggcag aaaagctgtt aaacagggag tggtaaacct   14880
tgtcaaatat gccaaataac aatggcaagc agcagaagag aaagaagggg gatggccagc   14940
cagtcaatca gctgtgccag atgctgggta agatcatcgc tcagcaaaac cagtccagag   15000
gcaagggacc gggaaagaaa aataagaaga aaacccggga gaagccccat tttcctctag   15060
cgactgaaga tgatgtcaga catcacttta cccctagtga gcggcaattg tgtctgtcgt   15120
caatccagac cgcctttaat caaggcgctg ggacttgcac cctgtcagat tcaggaggga   15180
taagttacac tgtggagttt agtttgccta cgcatcatac tgtgcgcctg atccgcgtca   15240
cagcatcacc ctcagcatga tgggctggca ttcttgaggc atctcagtgt ttgaattgga   15300
```

```
-continued agaatgtgtg gtgaatggca ctgattgaca ttgtgcctct aagtcaccta ttcaattagg     15360
gcgaccgtgt gggggtgaga tttaattggc gagaaccatg cggccgaaat taaaaaaaaa     15420
aaaaaaaaaa aaaaaaaaaa aaaaaaaaaa aaaaaaaaaa aaaaaagaa                15470

<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
tcaattcagg cctaaagttg                                                    20

<210> SEQ ID NO 18
<211> LENGTH: 23
<212> TYPE: DNA
<213> ORGANISM: artificial sequence
<220> FEATURE:
<223> OTHER INFORMATION: primer

<400> SEQUENCE: 18
cgccctaatt gaataggtga ctt                                                23
```